(12) United States Patent
Kobayashi et al.

(10) Patent No.: US 10,447,939 B2
(45) Date of Patent: Oct. 15, 2019

(54) ENDOSCOPE APPARATUS, METHOD OF OPERATING ENDOSCOPE APPARATUS, AND RECORDING MEDIUM

(71) Applicant: OLYMPUS CORPORATION, Tokyo (JP)

(72) Inventors: Eiichi Kobayashi, Tokyo (JP); Yutaka Konomura, Tokyo (JP); Masayoshi Yokota, Tokyo (JP); Kiyotomi Ogawa, Tokyo (JP)

(73) Assignee: Olympus Coproration, Tokyo (JP)

( * ) Notice: Subject to any disclaimer, the term of this patent is extended or adjusted under 35 U.S.C. 154(b) by 0 days.

(21) Appl. No.: 15/949,149

(22) Filed: Apr. 10, 2018

(65) Prior Publication Data

US 2018/0227476 A1    Aug. 9, 2018

Related U.S. Application Data

(63) Continuation of application No. PCT/JP2016/079453, filed on Oct. 4, 2016.

(30) Foreign Application Priority Data

Oct. 16, 2015   (JP) .................................. 2015-204495

(51) Int. Cl.
*H04N 5/235* (2006.01)
*A61B 1/00* (2006.01)
(Continued)

(52) U.S. Cl.
CPC ....... *H04N 5/2352* (2013.01); *A61B 1/00006* (2013.01); *A61B 1/00009* (2013.01);
(Continued)

(58) Field of Classification Search
CPC ........................... H04N 5/3532; H04N 5/2352
See application file for complete search history.

(56) References Cited

U.S. PATENT DOCUMENTS

| 6,864,916 B1 * | 3/2005 | Nayar .................. H04N 5/2355 348/224.1 |
| 8,189,069 B2 * | 5/2012 | Ogawa ............... H04N 5/23232 348/229.1 |

(Continued)

FOREIGN PATENT DOCUMENTS

| EP | 2698985 A1 | 2/2014 |
| JP | 2002-049083 A | 2/2002 |

(Continued)

OTHER PUBLICATIONS

International Search Report dated Dec. 27, 2016 issued in PCT/JP2016/079453.

*Primary Examiner* — James M Pontius
(74) *Attorney, Agent, or Firm* — Scully Scott Murphy & Presser, P.C.

(57) ABSTRACT

An endoscope apparatus includes an imaging element, a video signal generating circuit, an illuminator, and one or more controllers. An imaging area in which a plurality of pixels are disposed includes a scanning area. In a case in which a first operation mode is set, the one or more controllers control the imaging element such that at least parts of the exposure periods of the pixels disposed in at least a part of the scanning area overlap each other. In a case in which a second operation mode is set, the one or more controllers control the illuminator such that the light source is turned on in a period in which at least parts of the exposure periods of the pixels disposed in at least a part of the scanning area overlap each other.

22 Claims, 18 Drawing Sheets

(51) Int. Cl.

| | | |
|---|---|---|
| *A61B 1/045* | (2006.01) | |
| *A61B 1/05* | (2006.01) | |
| *A61B 1/06* | (2006.01) | |
| *H04N 5/225* | (2006.01) | |
| *H04N 5/232* | (2006.01) | |
| *H04N 5/353* | (2011.01) | |
| *H04N 5/3745* | (2011.01) | |
| *G02B 23/24* | (2006.01) | |
| *H04N 7/18* | (2006.01) | |
| *H04N 5/243* | (2006.01) | |
| *H04N 13/00* | (2018.01) | |

(52) U.S. Cl.
  CPC .......... *A61B 1/00045* (2013.01); *A61B 1/045* (2013.01); *A61B 1/051* (2013.01); *A61B 1/0676* (2013.01); *G02B 23/2484* (2013.01); *H04N 5/2256* (2013.01); *H04N 5/2353* (2013.01); *H04N 5/2354* (2013.01); *H04N 5/23245* (2013.01); *H04N 5/23254* (2013.01); *H04N 5/23293* (2013.01); *H04N 5/243* (2013.01); *H04N 5/3532* (2013.01); *H04N 5/37457* (2013.01); *H04N 7/183* (2013.01); *H04N 13/00* (2013.01); *A61B 1/00055* (2013.01); *H04N 2005/2255* (2013.01)

(56) References Cited

U.S. PATENT DOCUMENTS

| | | | |
|---|---|---|---|
| 2004/0183921 A1* | 9/2004 | Ueda | G01N 21/6458 348/222.1 |
| 2004/0214099 A1* | 10/2004 | Matsumoto | H04N 1/1903 430/24 |
| 2008/0219585 A1* | 9/2008 | Kasai | H04N 5/2351 382/274 |
| 2009/0043162 A1 | 2/2009 | Takahashi | |
| 2009/0086073 A1* | 4/2009 | Kobayashi | H04N 5/3597 348/302 |
| 2010/0128159 A1* | 5/2010 | Yamashita | H04N 5/35563 348/311 |
| 2011/0285897 A1* | 11/2011 | Fujii | G03B 7/093 348/345 |
| 2013/0050456 A1 | 2/2013 | Sakurai et al. | |
| 2018/0097984 A1* | 4/2018 | Kobayashi | H04N 5/35581 |

FOREIGN PATENT DOCUMENTS

| | | |
|---|---|---|
| JP | 2006-325741 A | 12/2006 |
| JP | 2009-039432 A | 2/2009 |
| JP | 2013-046672 A | 3/2013 |
| JP | 2013-118698 A | 6/2013 |
| JP | 2014-153655 A | 8/2014 |
| JP | 2014-204198 A | 10/2014 |
| WO | WO 2013/157368 A1 | 10/2013 |

\* cited by examiner

ENDOSCOPE APPARATUS, METHOD OF OPERATING ENDOSCOPE APPARATUS, AND RECORDING MEDIUM

Priority is claimed on Japanese Patent Application No. 2015-204495, filed on Oct. 16, 2015, and the present application is a continuation application based on PCT/JP 2016/079453 filed on Oct. 4, 2016, and the contents of the Japanese Patent Application and the PCT application described above are incorporated herein by reference.

BACKGROUND

Technical Field

The present invention relates to an endoscope apparatus, a method of operating an endoscope apparatus, and a recording medium.

Background Art

Endoscope apparatuses performing three-dimensional measurement for a subject on the basis of images of the subject acquired by an endoscope are used. For example, an endoscope apparatus performing stereo measurement on the basis of two images having a parallax is disclosed in Japanese Unexamined Patent Application, First Publication No. 2006-325741. In the endoscope apparatus disclosed in Japanese Unexamined Patent Application, First Publication No. 2006-325741, a distance to a subject at a designated position on one of two images acquired in real time is displayed in real time.

As a general method of driving an imaging element used for an endoscope apparatus, there is a rolling shutter. The imaging element includes a plurality of pixels disposed in a matrix pattern. In the rolling shutter, the generation of an imaging signal and the reading thereof are performed for each row in the arrangement of the plurality of pixels.

SUMMARY

According to a first aspect of the present invention, an endoscope apparatus includes an imaging element, a video signal generating circuit, an illuminator, and one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels of each row in the scanning area. The video signal generating circuit generates video signals from the imaging signals. The illuminator includes a light source generating illumination light emitted to the subject. The one or more controllers control the imaging element and the illuminator in accordance with a set operation mode among a plurality of operation modes. The plurality of operation modes include a first operation mode and a second operation mode. In a case in which the first operation mode is set, the one or more controllers control the illuminator such that the light source is continuously controlled to be turned on in exposure periods of all of the pixels disposed in the scanning area. In a case in which the second operation mode is set, the one or more controllers control the imaging element such that at least parts of the exposure periods of the pixels disposed in at least a part of the scanning area overlap each other. In a case in which the second operation mode is set, the one or more controllers control the illuminator such that the light source is turned on in a period in which at least parts of the exposure periods of the pixels disposed in at least a part of the scanning area overlap each other.

According to a second aspect of the present invention, in the first aspect, the one or more controllers may control at least one of a scanning rate, a scanning area, a scanning start timing, an exposure time, and a gain in accordance with the set operation mode.

According to a third aspect of the present invention, in the first aspect, the one or more controllers may control at least one of a turning-on timing, a turning-on time, and a light quantity of the light source in accordance with the set operation mode.

According to a fourth aspect of the present invention, in the first aspect, the illuminator may include a plurality of the independent light sources. The one or more controllers may select the light source that will generate the illumination light in accordance with the set operation mode.

According to a fifth aspect of the present invention, in any one of the first to fourth aspect, the one or more controllers may execute a measurement process on the basis of the video signal. The plurality of operation modes may include an operation mode in which at least the measurement process is executed.

According to a sixth aspect of the present invention, in the fifth aspect, the second operation mode may be the operation mode in which at least the measurement process is executed.

According to a seventh aspect of the present invention, in the fifth aspect, a method of driving the imaging element may be a rolling shutter. The video signal generating circuit may generate the video signals by amplifying the imaging signals with a predetermined gain. The scanning area may include a first area and a second area. The first area may be an area in which a length of a period, in which the illumination light is emitted to the subject in the exposure period, is a first time. The second area may be an area in which a length of a period, in which the illumination light is emitted to the subject in the exposure period, is a second time that is shorter than the first time. A second gain may have a value calculated by dividing the first time by the second time and multiplying a quotient thereof by a first gain. The second gain may be a gain when the imaging signals read from the pixels disposed in the second area are amplified by the video signal generating circuit. The first gain may be a gain when the imaging signals read from the pixels disposed in the first area are amplified by the video signal generating circuit.

According to an eighth aspect of the present invention, in the fifth aspect, a method of driving the imaging element may be a rolling shutter. The imaging element may further include a signal processing circuit that amplifies the imaging signals output from the plurality of pixels with a predetermined gain. The scanning area includes a first area and a second area. The first area is an area in which a length of a period, in which the illumination light is emitted to the subject in the exposure period, is a first time. The second area is an area in which a length of a period, in which the illumination light is emitted to the subject in the exposure period, is a second time that is shorter than the first time. A second gain may have a value calculated by dividing the first time by the second time and multiplying a quotient thereof by a first gain. The second gain is a gain when the imaging signals read from the pixels disposed in the second area are amplified by the signal processing circuit. The first gain is a gain when the imaging signals read from the pixels disposed in the first area are amplified by the signal processing circuit.

According to a ninth aspect of the present invention, in the fifth aspect, the one or more controllers may control the illuminator such that the light source is turned on in a period in which at least parts of the exposure periods of all of the pixels disposed in the scanning area overlap each other, and such that periods in which the illumination light is emitted to the subject in all of the pixels disposed in the scanning area in the exposure periods are the same.

According to a tenth aspect of the present invention, in the fifth aspect, the one or more controllers may control the illuminator such that the light source is intermittently turned on plural times, and such that at least parts of the exposure periods of the pixels disposed in at least a part of the scanning area overlap each other in each period of the plural times of turning-on.

According to an eleventh aspect of the present invention, in the tenth aspect, the one or more controllers may control the illuminator such that light quantities of the illumination light in the plural times of turning-on are the same.

According to a twelfth aspect of the present invention, in the eleventh aspect, in a case in which an emission time is completely included in the exposure periods of first pixels of the scanning area and only a part of the emission time is included in the exposure periods of second pixels of the scanning area, the one or more controllers may control the illuminator such that a first time and a second time are the same. The second pixels are different from the first pixels. The emission time is a length of a period in which the illumination light is emitted to the subject in accordance with intermittent turning-on of the light source once. The first time is a length of a period in which the illumination light is emitted to the subject in accordance with intermittent turning-on of the light source once in the exposure periods of the first pixels. The second time is a sum of a plurality of lengths of periods in which the illumination light is emitted to the subject in accordance with plural times of intermittent turning-on of the light source in the exposure periods of the second pixels.

According to a thirteenth aspect of the present invention, in the twelfth aspect, the endoscope apparatus may further include a motion detector and a warning generator. The motion detector detects moving of the subject on the basis of the imaging signals read from the second pixels or the video signal generated from the imaging signals read from the second pixels. The warning generator generates a warning in a case in which the amount of the moving of the subject is equal to or greater than a predetermined amount.

According to a fourteenth aspect of the present invention, in the fifth aspect, the one or more controllers may set the scanning area to include the pixel at which a measurement point is set in a case in which the operation mode in which at least the measurement process is executed is set.

According to a fifteenth aspect of the present invention, in any one of the first to fourth aspects, the one or more controllers may set a plurality of the scanning areas. The imaging element may generate the imaging signals of the pixels included in each of the plurality of the scanning areas. The video signal generating circuit may generate the video signal by composing the imaging signals of the pixels included in each of the plurality of the scanning areas.

According to a sixteenth aspect of the present invention, in the fifteenth aspect, the one or more controllers may execute a measurement process on the basis of the video signal. The plurality of operation modes may include an operation mode in which at least the measurement process is executed. In a case in which the operation mode in which at least the measurement process is executed is set and a plurality of measurement points are set, the one or more controllers may set each of the plurality of the scanning areas to include the pixel at which each of the plurality of measurement points is set.

According to a seventeenth aspect of the present invention, in any one of the first to third aspects, the illuminator may include a plurality of the light sources each including a measurement light source used for projecting a pattern onto the subject. The one or more controllers may execute a measurement process on the basis of the video signal. The plurality of operation modes may include an operation mode in which at least the measurement process is executed. In a case in which the operation mode in which at least the measurement process is executed is set, the one or more controllers may turn on the measurement light source.

According to an eighteenth aspect of the present invention, in the fifth aspect, in a case in which the operation mode in which at least the measurement process is executed is set, the one or more controllers may control a first scanning rate to be larger than a second scanning rate. The first scanning rate is a scanning rate for reading the imaging signals used for the measurement process from the pixels. The second scanning rate is a scanning rate for reading the imaging signals used only for a process other than the measurement process from the pixels.

According to a nineteenth aspect of the present invention, in any one of the first to fourth aspects, the endoscope apparatus may further include a display. The one or more controllers may execute a measurement process on the basis of the video signal. The display displays an image of the subject. The plurality of operation modes may include an operation mode in which at least image display and the measurement process are executed. In a case in which the operation mode in which at least the image display and the measurement process are executed is set, the one or more controllers may control the imaging element to alternately output a first imaging signal and a second imaging signal. The first imaging signal is for one image used for the image display. The second imaging signal is for one or more images used for the measurement process. The display may display the one image on the basis of the video signal generated from the first imaging signal. The one or more controllers may execute the measurement process on the basis of the video signal generated from the second imaging signal and corresponding to the one or more images.

According to a twentieth aspect of the present invention, in the nineteenth aspect, the one or more controllers may control the imaging element to output the first imaging signal in a first display period and output the second imaging signal in a second display period following the first display period. The first display period and the second display period may be based on a display period of the display. The display may display the one image on the basis of the video signal generated from the first imaging signal in the first display period and the second display period.

According to a twenty first aspect of the present invention, a method of operating an endoscope apparatus includes a first step, a second step, and a third step. The endoscope apparatus includes an imaging element, a video signal generating circuit, an illuminator, and one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels of each row in the scanning area. The video signal generating circuit generates video signals from the imaging signals. The illuminator includes a light source generating illumination light emitted to the subject. The one or more controllers control the imaging element in accordance with a set operation mode among a plurality of operation modes. The one or more controllers control the illuminator in accordance with the set operation mode. The plurality of operation modes include a first operation mode and a second operation mode. In a case in which the first operation mode is set, the one or more controllers control the illuminator such that the light source is continuously controlled to be turned on in exposure periods of all of the pixels disposed in the scanning area in the first step. In a case in which the second operation mode is set, the one or more controllers control the imaging element such that at least parts of the exposure periods of the pixels disposed in at least a part of the scanning area overlap each other in the second step. In a case in which the second operation mode is set, the one or more controllers control the illuminator such that the light source is turned on in a period in which at least parts of the exposure periods of the pixels disposed in at least a part of the scanning area overlap each other in the third step.

According to a twenty second aspect of the present invention, a non-transitory computer-readable recording medium having a program for causing one or more controllers of an endoscope apparatus to execute a first step, a second step, and a third step recorded thereon is provided. The endoscope apparatus includes: an imaging element; a video signal generating circuit; an illuminator; and the one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels of each row in the scanning area. The video signal generating circuit generates video signals from the imaging signals. The illuminator includes a light source generating illumination light emitted to the subject. The one or more controllers control the imaging element and the illuminator in accordance with a set operation mode among a plurality of operation modes. The plurality of operation modes include a first operation mode and a second operation mode. In a case in which the first operation mode is set, the one or more controllers control the illuminator such that the light source is continuously controlled to be turned on in exposure periods of all of the pixels disposed in the scanning area in the first step. In a case in which the second operation mode is set, the one or more controllers control the imaging element such that at least parts of the exposure periods of the pixels disposed in at least a part of the scanning area overlap each other in the second step. In a case in which the second operation mode is set, the one or more controllers control the illuminator such that the light source is turned on in a period in which at least parts of the exposure periods of the pixels disposed in at least a part of the scanning area overlap each other in the third step.

DETAILED DESCRIPTION OF THE PREFERRED EMBODIMENT

Figure 1:
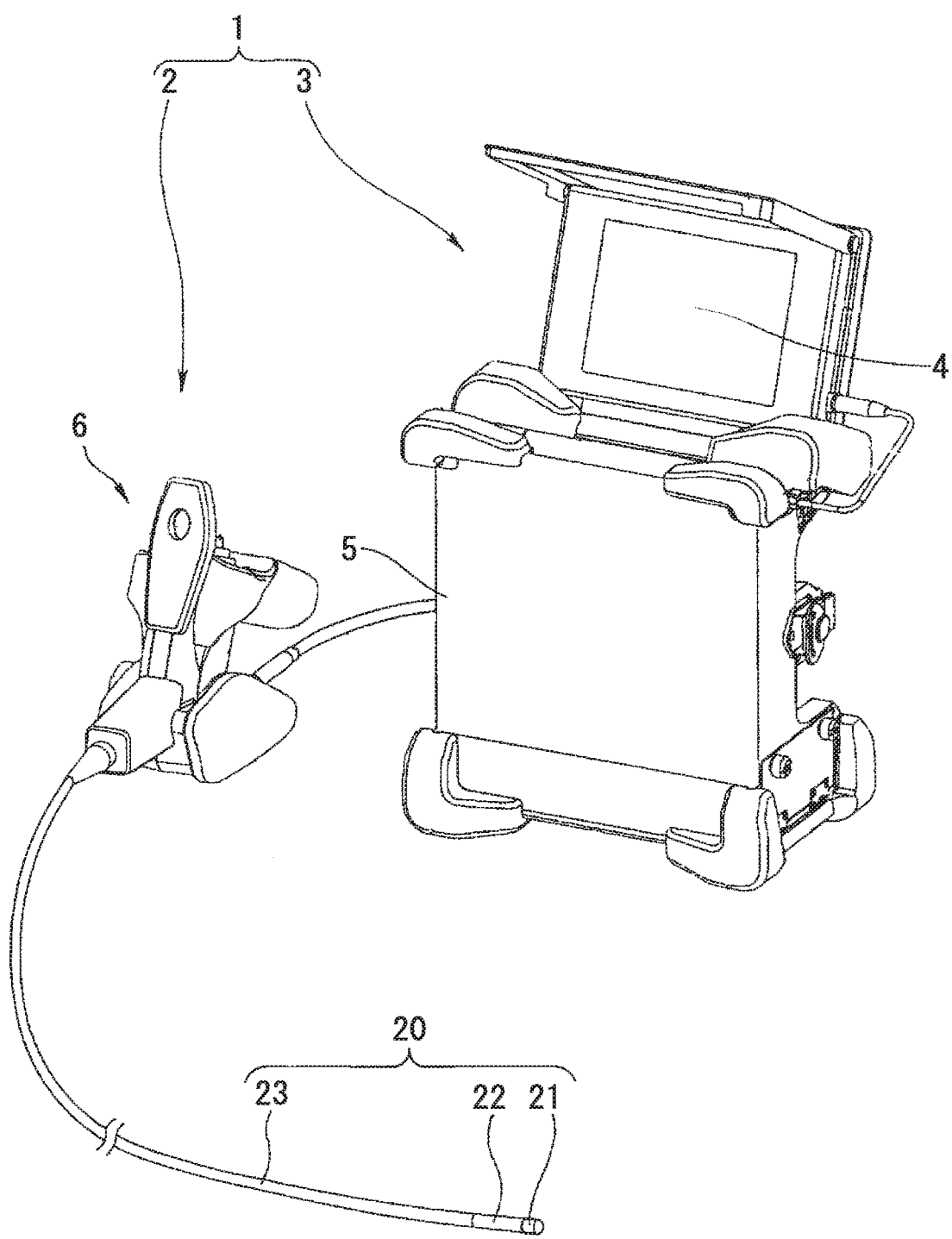
FIG. 1 is a perspective view showing the entire configuration of an endoscope apparatus according to an embodiment of the present invention.
Figure 2:
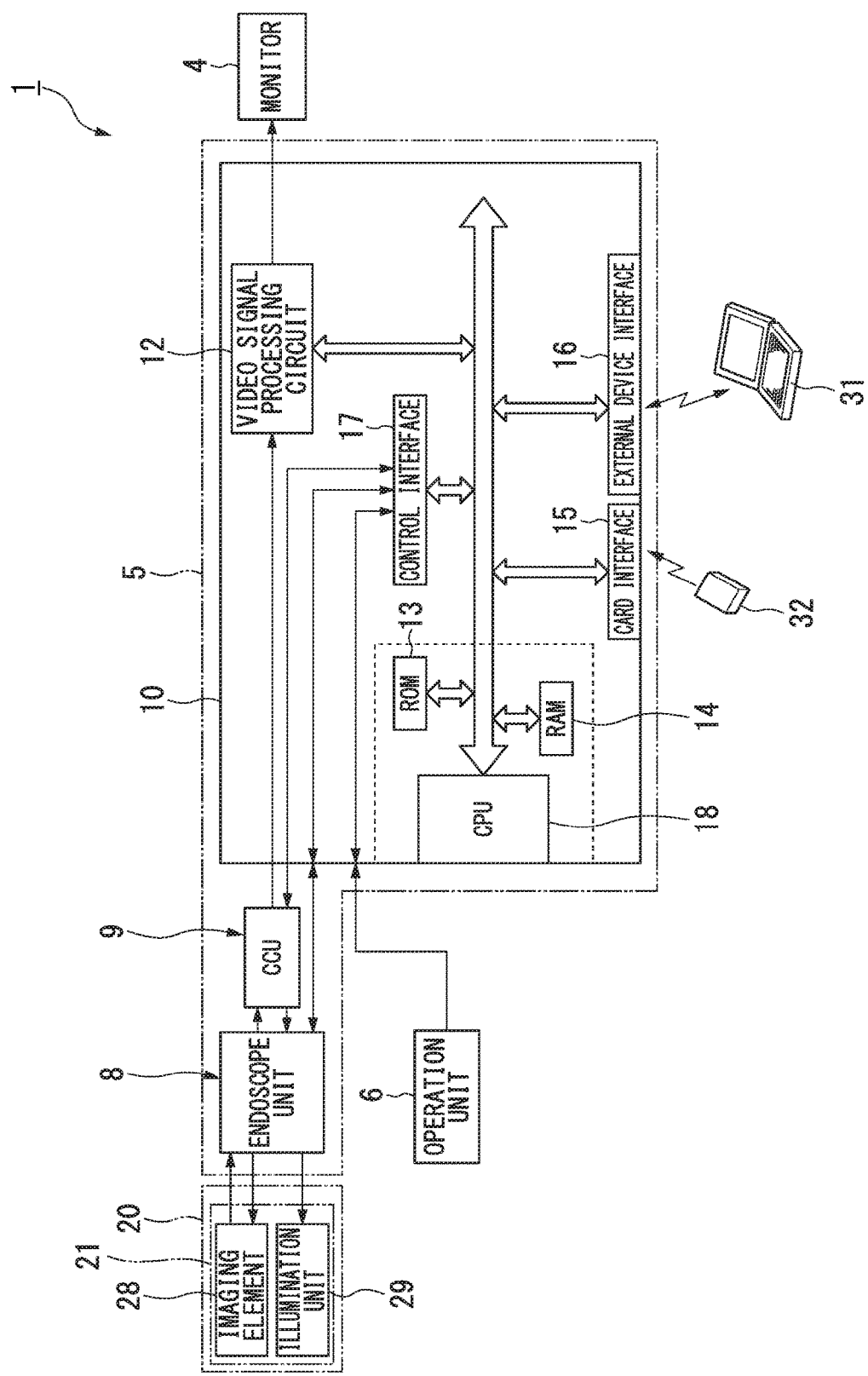
FIG. 2 is a block diagram showing the internal configuration of an endoscope apparatus according to an embodiment of the present invention.

Hereinafter, an embodiment of the present invention will be described with reference to the drawings. FIG. 1 shows the entire configuration of an endoscope apparatus 1 according to a first embodiment of the present invention. FIG. 2 shows the internal configuration of the endoscope apparatus 1. As shown in FIG. 1, the endoscope apparatus 1 includes an endoscope 2 and a main body 3. The endoscope 2 includes an elongated insertion unit 20 and an operation unit 6 used for a user to perform a necessary operation for controlling the entire apparatus. The main body 3 is connected to the endoscope 2. The main body 3 includes a monitor 4 and a casing 5. The monitor 4 displays an image of a subject captured by the endoscope 2, an operation menu, and the like. The casing 5 includes a main control unit 10 (see FIG. 2) on the inside thereof.

The insertion unit 20 is inserted into the inside of a test object. The insertion unit 20 includes, a rigid tip end part 21, a bending part 22 that can be bent, and a flexible tube part 23 that has flexibility. The tip end part 21 is disposed on the tip end side of the insertion unit 20. The flexible tube part 23 is disposed on the main body side of the insertion unit 20. The bending part 22 is disposed between the tip end part 21 and the flexible tube part 23. An optical adaptor for forming a subject image can be detachably attached to the tip end part 21.

As shown in FIG. 2, the tip end part 21 includes an imaging element 28 and an illumination unit 29 (illuminator). The imaging element 28 executes photoelectric conversion of a subject image formed through the optical adaptor to generate an imaging signal. For example, the imaging element 28 is a complementary metal oxide semiconductor (CMOS) image sensor. The imaging element 28 includes a plurality of pixels disposed in a matrix pattern. The operations of the plurality of pixels are controlled for each row of the arrangement of the plurality of pixels.

The illumination unit 29 includes a light source that generates illumination light emitted to a subject. For example, the light source is a light emitting diode (LED). The illumination unit 29 may be disposed inside the casing 5, and illumination light generated by the illumination unit 29 may be guided by a light guide to the tip end part 21.

The casing 5 includes an endoscope unit 8, a camera control unit (CCU) 9, and a main control unit 10. The endoscope unit 8 includes a light source driving device that drives the light source of the illumination unit 29 and a bending device that bends the bending part 22. The CCU 9 drives the imaging element 28. An imaging signal output from the imaging element 28 is input to the CCU 9. The CCU 9 executes a pre-process including amplification, noise elimination, and the like for an imaging signal acquired by the imaging element 28. The CCU 9 converts the imaging signal for which the pre-process has been executed into a video signal such as an NTSC signal.

The main control unit 10 includes: a video signal processing circuit 12, a read only memory (ROM) 13; a random access memory (RAM) 14; a card interface 15; an external device interface 16; a control interface 17; and a central processing unit (CPU) 18.

The video signal processing circuit 12 executes predetermined video processing for a video signal output from the CCU 9. For example, the video signal processing circuit 12 may compose a video signal output from the CCU 9 and an image of an operation screen or measurement information generated by the CPU 18. The video signal processing circuit 12 outputs the composed video signal to the monitor 4.

The ROM 13 is a nonvolatile recording medium in which a program used for the CPU 18 to control the operation of the endoscope apparatus 1 is recorded. The RAM 14 is a volatile recording medium in which information used by the CPU 18 for controlling the endoscope apparatus 1 is temporarily stored. The CPU 18 controls the operation of the endoscope apparatus 1 on the basis of a program recorded in the ROM 13. The CPU 18 may drive the imaging element 28 not through the CCU 9.

A memory card 32 that is an attachable and detachable recording medium is connected to the card interface 15. The card interface 15 obtains control processing information, image information, and the like stored in the memory card 32 into the main control unit 10. In addition, the card interface 15 records the control processing information, the image information, and the like generated by the endoscope apparatus 1 in the memory card 32.

An external device such as a USB device is connected to the external device interface 16. For example, a personal computer 31 is connected to the external device interface 16. The external device interface 16 transmits information to the personal computer 31 and receives information from the personal computer 31. Accordingly, the monitor of the personal computer 31 can display information. In addition, a user can perform an operation regarding the control of the endoscope apparatus 1 through the personal computer 31.

The control interface 17 communicates with the operation unit 6, the endoscope unit 8, and the CCU 9 for operation control. The control interface 17 notifies the CPU 18 of an instruction input by a user through the operation unit 6. The control interface 17 outputs a control signal used for controlling the illumination unit 29 to the endoscope unit 8. The control interface 17 outputs a control signal used for controlling the imaging element 28 to the CCU 9. In a case in which the CPU 18 controls the imaging element 28 not through the CCU 9, the control interface 17 outputs a control signal used for controlling the imaging element 28 to the imaging element 28.

A program executed by the CPU 18 may be recorded in a computer-readable recording medium. The program recorded in this recording medium may be read by a computer other than the endoscope apparatus 1 and executed. For example, the personal computer 31 may read and execute the program. The personal computer 31 may control the endoscope apparatus 1 by transmitting control information used for controlling the endoscope apparatus 1 to the endoscope apparatus 1 in accordance with a program. Alternatively, the personal computer 31 may acquire a video signal from the endoscope apparatus 1 and execute measurement using the acquired video signal.

The program described above may be transmitted from a computer including a storage device in which this program is stored and the like to the endoscope apparatus 1 through a transmission medium or a transmission wave in a transmission medium. The "transmission medium" transmitting a program is a medium having a function of transmitting information such as a network (communication network) including the Internet or a communication circuit line (communication line) such as a telephone circuit line. In addition, the program described above may realize a part of the functions described above. Furthermore, the program described above may be a differential file (differential program) that can realize the functions described above by being combined with a program that is already recorded in the computer.

Figure 3:
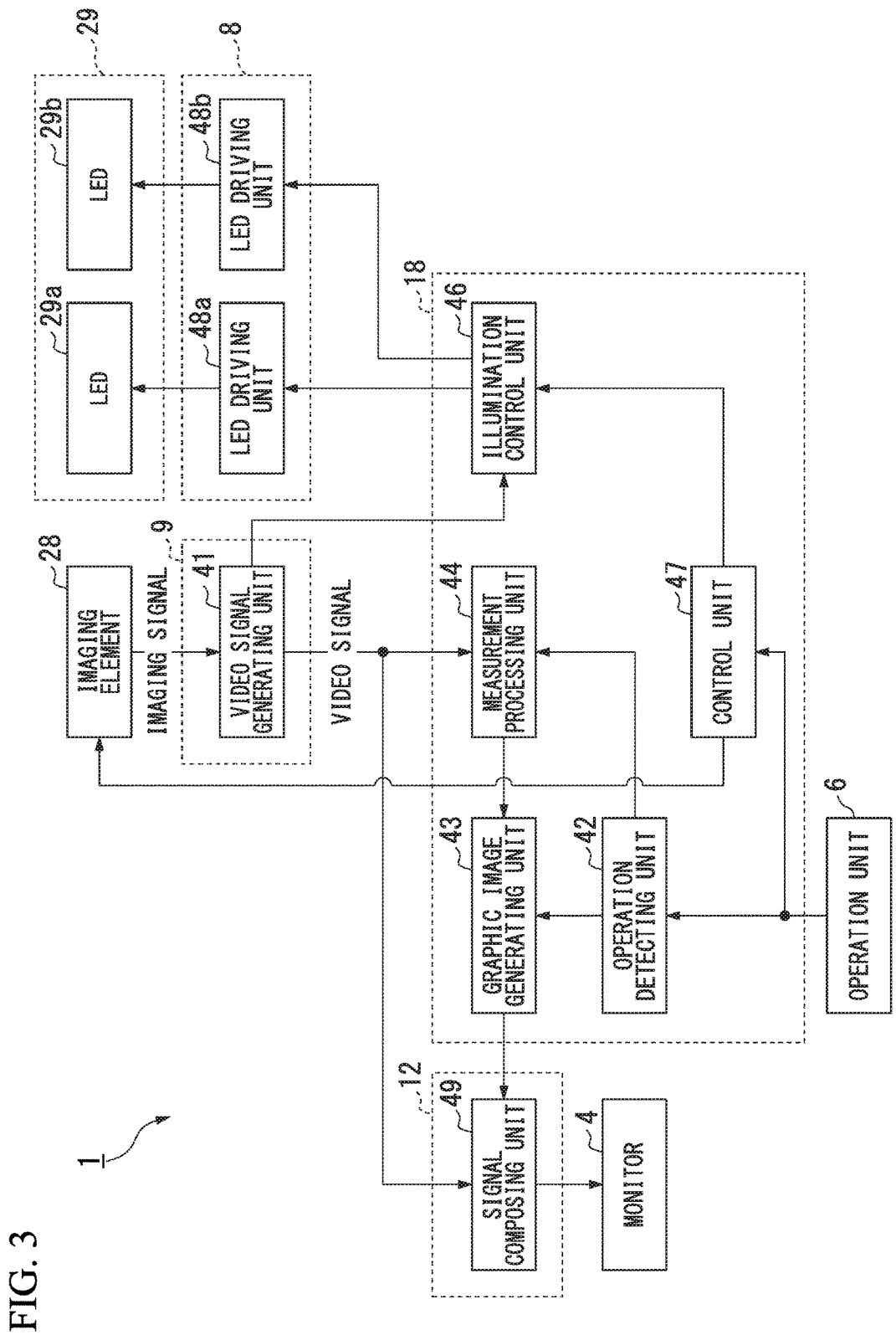
FIG. 3 is a block diagram showing a configuration regarding major functions of an endoscope apparatus according to an embodiment of the present invention.

FIG. 3 is a block diagram showing a configuration regarding major functions of the endoscope apparatus 1. As shown in FIG. 3, the endoscope apparatus 1 includes a monitor 4 (display), an operation unit 6, an imaging element 28, an LED 29a, an LED 29b, a video signal generating unit 41 (video signal generating circuit), an operation detecting unit 42, a graphic image generating unit 43, a measurement processing unit 44, an illumination control unit 46, a control unit 47, an LED driving unit 48a, an LED driving unit 48b, and a signal composing unit 49.

The illumination unit 29 includes the LED 29a and the LED 29b that are light sources. The LED 29a is a light source used for observation and stereo measurement. For example, the LED 29b may be a light source used for projecting a pattern onto a subject. In the stereo measurement, a matching process of detecting corresponding positions of two images having parallax is executed. In a case in which there are small features on the surface of a subject, the accuracy of the matching process easily decreases. By projecting a pattern onto a subject, the accuracy of the matching process is improved. The LED 29b may be a light source used for projecting stripes onto a subject. The endoscope apparatus 1 may execute three-dimensional measurement using a phase shift method. In the phase shift method, a pattern formed by parallel stripes is projected onto the surface of a subject. The position of the stripes changes temporally. Three-dimensional measurement is executed on the basis of a change in the luminance of each pixel of a subject image.

The light source of the illumination unit 29 may be a light source other than an LED. The illumination unit 29 may include only one light source or three or more light sources.

The video signal generating unit 41 corresponds to the function of the CCU 9. The video signal generating unit 41 generates a video signal from an imaging signal output from the imaging element 28. The video signal generating unit 41 executes a preprocess including amplification, noise elimination, and the like for the imaging signal and converts the imaging signal into a video signal.

The operation detecting unit 42, the graphic image generating unit 43, the measurement processing unit 44, the illumination control unit 46, and the control unit 47 correspond to functions of the CPU 18. The operation detecting unit 42 detects a user's operation for the operation unit 6. The operation detecting unit 42 sets a display position of a target displayed on the screen of the monitor 4 in accordance with operation details. The target represents the position of a measurement point. A user can move the target inside the screen by operating the operation unit 6.

The graphic image generating unit 43 generates a graphic image signal corresponding to an operation menu and measurement information displayed on the screen of the monitor 4. The measurement information includes an image of the target and measurement results. As described above, the display position of the target inside the screen is set by the operation detecting unit 42. The measurement processing unit 44 executes a measurement process on the basis of a video signal generated by the video signal generating unit 41. In the measurement process, an object distance, a length, an area, and the like are calculated. The object distance is a distance from the tip end part 21 to a subject.

The illumination control unit 46 outputs a control signal used for controlling the illumination unit 29. In this way, the illumination control unit 46 controls the illumination unit 29. There are many cases in which the inside of a target object for observation or measurement in which the insertion unit 20 is inserted is dark. For this reason, the illumination control unit 46 turns on the illumination unit 29 when a subject is imaged.

The video signal generating unit 41 detects the position of a row in which an imaging signal is read on the basis of an imaging signal output from the imaging element 28. The video signal generating unit 41 notifies the illumination control unit 46 of the position of the row that has been detected. The illumination control unit 46 controls the operation timing of the illumination unit 29 using a timing at the position of the row notified from the video signal generating unit 41 as a reference. The illumination control unit 46 may control the operation timing of the illumination unit 29 using the operation timing of the imaging element 28 determined by the control unit 47 as a reference.

The control unit 47 controls assignment of processes to the operation detecting unit 42, the graphic image generating unit 43, the measurement processing unit 44, and the illumination control unit 46 and controls the overall operation of the endoscope apparatus 1. In addition, the control unit 47 outputs a control signal used for controlling the imaging element 28. This control signal is transmitted to the imaging element 28 through the CCU 9 and the endoscope unit 8. Alternatively, this control signal is directly transmitted to the imaging element 28. In this way, the control unit 47 controls the imaging element 28 in accordance with an operation mode set in the endoscope apparatus 1. The operation mode of the endoscope apparatus 1 will be described later.

The LED driving unit 48a and the LED driving unit 48b correspond to functions of the endoscope unit 8. The LED driving unit 48a outputs a driving signal used for driving the LED 29a on the basis of a control signal output from the illumination control unit 46. The LED 29a generates illumination light on the basis of a driving signal output from the LED driving unit 48a. The LED driving unit 48b outputs a driving signal used for driving the LED 29b on the basis of a control signal output from the illumination control unit 46. The LED 29b generates illumination light on the basis of a driving signal output from the LED driving unit 48b.

The signal composing unit 49 corresponds to the function of the video signal processing circuit 12. The signal composing unit 49 composes a video signal generated by the video signal generating unit 41 and a graphic image signal generated by the graphic image generating unit 43. The monitor 4 displays an image on the basis of a video signal output from the signal composing unit 49.

The operation detecting unit 42, the graphic image generating unit 43, the measurement processing unit 44, the illumination control unit 46, and the control unit 47 may be constituted as a processor (controller). For example, the processor may be at least one of a CPU, a digital signal processor (DSP), and a graphics processing unit (GPU). The processor may be at least one of an application specific integrated circuit (ASIC) and a field-programmable gate array (FPGA). The operation detecting unit 42, the graphic image generating unit 43, the measurement processing unit 44, the illumination control unit 46, and the control unit 47 may include one or a plurality of processors.

Figure 4:
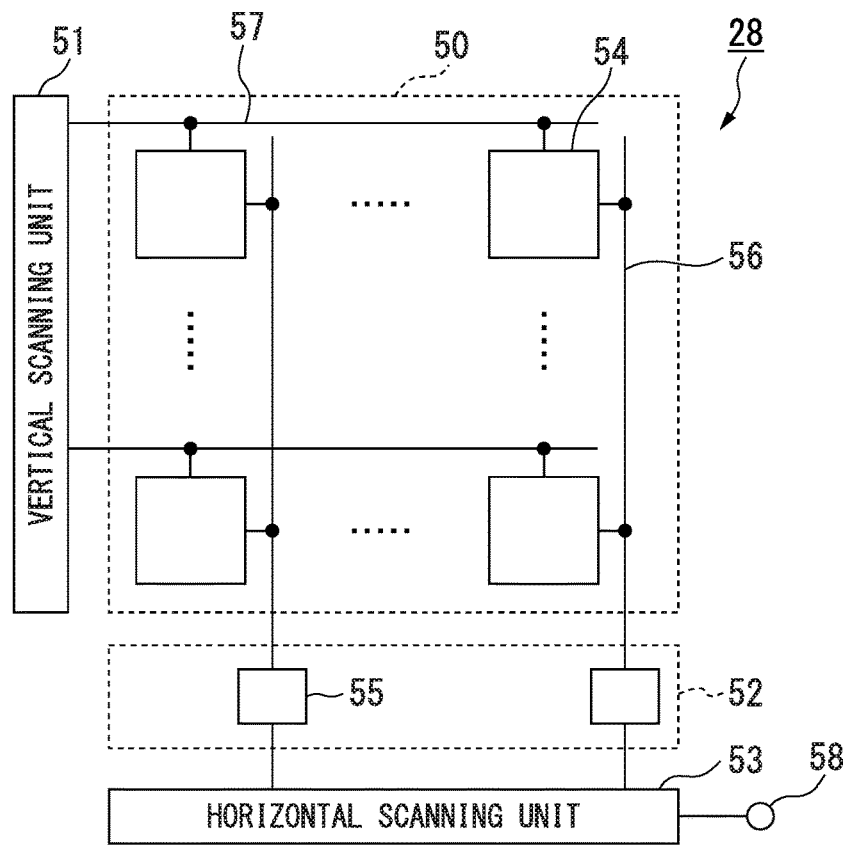
FIG. 4 is a block diagram showing the configuration of an imaging element of an endoscope apparatus according to an embodiment of the present invention.

FIG. 4 shows the configuration of the imaging element 28. As shown in FIG. 4, the imaging element 28 includes a pixel unit 50, a vertical scanning unit 51, a signal processing unit 52, and a horizontal scanning unit 53.

The pixel unit 50 includes a plurality of pixels 54 disposed in a matrix pattern. The plurality of pixels 54 are disposed in an imaging area of the imaging element 28. Each of the number of rows and the number of columns of the arrangement of the plurality of pixels 54 is two or more. The number of rows and the number of columns need not be the same. Each of the plurality of pixels 54 generates an imaging signal according to the amount of light incident to the pixel 54. Each of the plurality of pixels 54 is connected to a vertical signal line 56. A plurality of vertical signal lines 56 are disposed. Each of the plurality of vertical signal lines 56 is disposed in one column of the arrangement of the plurality of pixels 54. Each of the plurality of pixels 54 outputs a generated imaging signal to the vertical signal line 56.

Each of the plurality of pixels 54 is connected to a control signal line 57. A plurality of control signal lines 57 are disposed. Each of the plurality of control signal lines 57 is disposed for each row of the arrangement of the plurality of pixels 54. Each of the plurality of control signal lines 57 is connected to the vertical scanning unit 51. Control signals used for controlling the operation of the plurality of pixels 54 are output from the vertical scanning unit 51 to the control signal lines 57. A plurality of control signal lines 57 are disposed for the pixels 54 of one row. In FIG. 4, one control signal line 57 is shown for the pixels 54 of one row, and the other control signal lines 57 are not shown. Details of the control signals will be described later.

The operations of the plurality of pixels 54 are controlled on the basis of control signals output to the control signal lines 57. A control signal for the pixels 54 of one row is supplied to be common to all of the pixels 54 in the row. For this reason, the same operation timing is set for two or more pixels 54 disposed in the same row. In other words, two or more pixels 54 disposed in the same row are simultaneously operated. Details of the configuration of the pixels 54 will be described later.

A control signal generated by the control unit 47 is transmitted to the imaging element 28 through the CCU 9 and the endoscope unit 8. Alternatively, a control signal generated by the control unit 47 is directly transmitted to the imaging element 28. The imaging element 28 receives the control signal. The vertical scanning unit 51 generates a control signal used for controlling the operations of the plurality of pixels 54 on the basis of a received control signal. The vertical scanning unit 51 generates a control signal for each of a plurality of rows of the arrangement of the plurality of pixels 54. The vertical scanning unit 51 outputs the generated control signal to the control signal line 57.

The signal processing unit 52 includes a plurality of signal processing circuits 55. The signal processing circuits 55 are disposed for each column of the arrangement of the plurality of pixels 54. The signal processing circuit 55 is connected to the vertical signal line 56. The signal processing circuit 55 executes signal processing including amplification, noise elimination, and the like for an imaging signal output to the vertical signal line 56. At least one of the signal processing circuit 55 and the video signal generating unit 41 (CCU 9) has only to execute signal processing for an imaging signal.

The imaging signal processed by the signal processing circuit 55 is input to the horizontal scanning unit 53. The horizontal scanning unit 53 sequentially selects columns of the arrangement of the plurality of pixels 54. An imaging signal for a column selected by the horizontal scanning unit 53 is output from an output terminal 58.

As described above, the endoscope apparatus 1 includes the imaging element 28, the video signal generating unit 41, the illumination unit 29, the control unit 47, and the illumination control unit 46. The imaging element 28 images a subject to generate an imaging signal. The video signal generating unit 41 generates a video signal from the imaging signal. The illumination unit 29 includes light sources (the LED 29a and the LED 29b) generating illumination light emitted to a subject. The control unit 47 controls the imaging element 28 in accordance with a set operation mode among a plurality of operation modes. The illumination control unit 46 controls the illumination unit 29 in accordance with the set operation mode.

The imaging element 28 includes a plurality of pixels 54 disposed in a matrix pattern. An imaging area in which the plurality of pixels 54 are disposed includes a scanning area. Imaging signals are read from at least a part of pixels 54 of each row in the scanning area. The plurality of operation modes includes a first operation mode and a second operation mode. In a case in which the first operation mode is set, the illumination control unit 46 controls the illumination unit 29 such that the light source is continuously controlled to be turned on in exposure periods of all of the pixels 54 disposed in the scanning area. In a case in which a predetermined operation mode is set, the control unit 47 controls the imaging element 28 such that at least parts of exposure periods of pixels 54 disposed in at least a part of the scanning area overlap each other. In a case in which a predetermined operation mode is set, the illumination control unit 46 controls the illumination unit 29 such that the light source is turned on in a period in which at least part of the exposure periods of pixels 54 disposed in at least a part of the scanning area overlap each other. Details of the control of the scanning area, the imaging element 28, and the illumination unit 29 will be described later.

Figure 5:
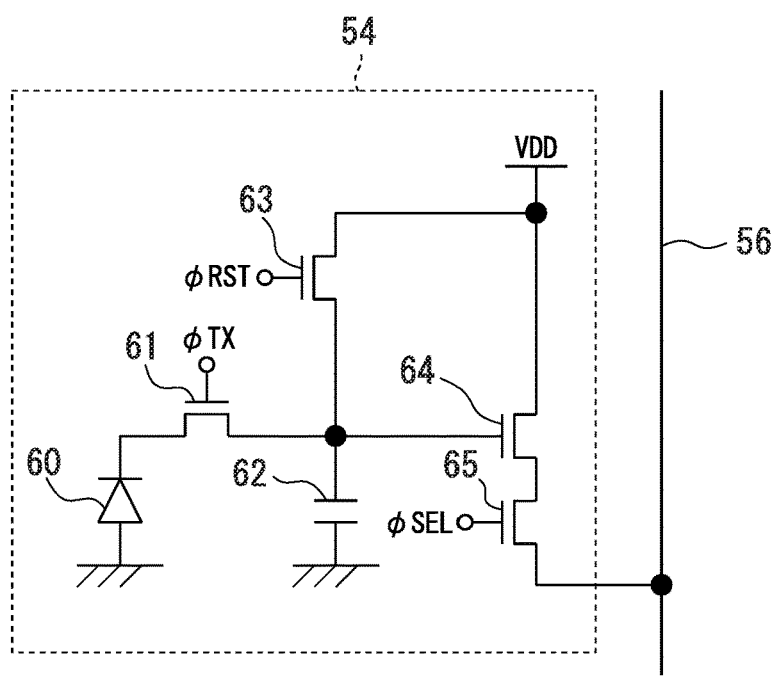
FIG. 5 is a circuit diagram showing the configuration of a pixel of an endoscope apparatus according to an embodiment of the present invention.

FIG. 5 is a circuit diagram showing the configuration of the pixel 54. As shown in FIG. 5, the pixel 54 includes a photoelectric conversion unit 60, an electric charge transmitting unit 61, an electric charge accumulating unit 62, a resetting unit 63, an amplification unit 64, and an output unit 65. The photoelectric conversion unit 60 is a photo diode. The electric charge accumulating unit 62 is a capacitor. For example, the electric charge accumulating unit 62 may be the capacitance of the gate of a transistor constituting the amplification unit 64. The electric charge transmitting unit 61, the resetting unit 63, the amplification unit 64, and the output unit 65 are transistors.

The photoelectric conversion unit 60 generates electric charge according to the amount of light incident to the pixel 54. The electric charge transmitting unit 61 transmits electric charge generated by the photoelectric conversion unit 60 to the electric charge accumulating unit 62. The electric charge accumulating unit 62 accumulates electric charge transmitted from the photoelectric conversion unit 60. The resetting unit 63 resets electric charge in the photoelectric conversion unit 60 and the electric charge accumulating unit 62 on the basis of a power source voltage VDD. By turning on the electric charge transmitting unit 61 and the resetting unit 63, the resetting unit 63 can reset the electric charge in the photoelectric conversion unit 60 and the electric charge accumulating unit 62. The amplification unit 64 amplifies a signal based on electric charge accumulated in the electric charge accumulating unit 62. The output unit 65 outputs the signal amplified by the amplification unit 64 to the vertical signal line 56 as an imaging signal.

The operation of the electric charge transmitting unit 61 is controlled using a control signal $\varphi TX$. The operation of the resetting unit 63 is controlled using a control signal $\varphi RST$. The operation of the output unit 65 is controlled using a control signal $\varphi SEL$. The control signal $\varphi TX$, the control signal $\varphi RST$, and the control signal $\varphi SEL$ are supplied from the vertical scanning unit 51 through the control signal lines 57.

The operation of the pixel 54 includes resetting, transmission of electric charge, and signal reading. The resetting corresponds to the operation of the resetting unit 63. The transmission of electric charge corresponds to the operation of the electric charge transmitting unit 61. The signal reading corresponds to the operation of the output unit 65.

Figure 6:
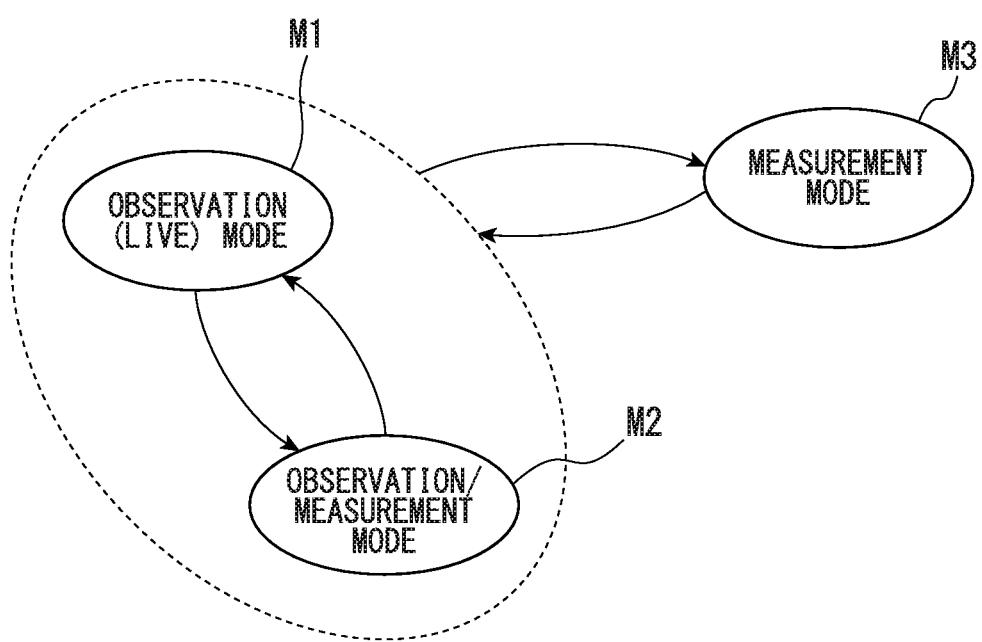
FIG. 6 is a reference diagram showing a plurality of operation mode of an endoscope apparatus according to an embodiment of the present invention.

FIG. 6 shows the plurality of operation modes of the endoscope apparatus 1. For example, the operation modes of the endoscope apparatus 1 include an observation (live) mode M1, an observation/measurement mode M2, and a measurement mode M3. In the observation mode M1, the endoscope apparatus 1 generates video signals by continuously imaging a subject and displays an image of the subject. In the observation/measurement mode M2, similar to the observation mode M1, the endoscope apparatus 1 executes generation of video signals and image display. In addition, in the observation/measurement mode M2, the endoscope apparatus 1 executes the measurement process on the basis of the video signals. For example, in the observation/measurement mode M2, the endoscope apparatus 1 measures an object distance and displays an image on which measurement results are superimposed. In the observation/measurement mode M2, the endoscope apparatus 1 repeatedly executes the generation of video signals, the image display, and the measurement process. In the observation mode M1 and the observation/measurement mode M2, a moving image of a subject is displayed. In the measurement mode M3, the endoscope apparatus 1 executes imaging of a subject one or more times and executes the measurement process on the basis of the video signals acquired by the imaging one or more times.

A user can change the operation mode set in the endoscope apparatus 1 by executing a predetermined operation for the operation unit 6. The predetermined operation is different according to an operation mode before change and an operation mode after change.

In a case in which a predetermined operation is executed for the operation unit 6 in a state in which the observation mode M1 is set in the endoscope apparatus 1, the operation mode set in the endoscope apparatus 1 is changed from the observation mode M1 to the observation/measurement mode M2. In a case in which a predetermined operation is executed for the operation unit 6 in a state in which the observation/measurement mode M2 is set in the endoscope apparatus 1, the operation mode set in the endoscope apparatus 1 is changed from the observation/measurement mode M2 to the observation mode M1. In a case in which a predetermined operation is executed for the operation unit 6 in a state in which the observation mode M1 or the observation/measurement mode M2 is set in the endoscope apparatus 1, the operation mode set in the endoscope apparatus 1 is changed from the observation mode M1 or the observation/measurement mode M2 to the measurement mode M3. In a case in which a predetermined operation is executed for the operation unit 6 in a state in which the measurement mode M3 is set in the endoscope apparatus 1, the operation mode set in the endoscope apparatus 1 is changed from the measurement mode M3 to the operation mode set before the setting of the measurement mode M3.

Information of the operation mode set in the endoscope apparatus 1 is stored in the RAM 14. The control unit 47 controls the operation of the endoscope apparatus 1 on the basis of the information of the operation mode stored in the RAM 14. In a case in which a change in the operation mode is directed in accordance with a predetermined operation for the operation unit 6, the control unit 47 changes the information of the operation mode stored in the RAM 14.

As described above, the endoscope apparatus 1 includes the measurement processing unit 44 that executes the measurement process on the basis of video signals. The plurality of operation modes include an operation mode in which at least the measurement process is executed. In the example described above, the operation mode in which at least the measurement process is executed includes the observation/measurement mode M2 and the measurement mode M3.

For example, the measurement processing unit 44 executes a measurement process based on the principle of stereo measurement. In the stereo measurement, an optical adapter forming a first optical image and a second optical image having parallax therebetween is used. The imaging element 28 generates an imaging signal based on the first optical image and the second optical image. The monitor 4 displays a first image corresponding to the first optical image and a second image corresponding to the second optical image. For example, the monitor 4 displays an image in which the first image and the second image are horizontally aligned.

A user operates a target on the screen of the monitor 4 through the operation unit 6, thereby designating a measurement point for one of the first image and the second image.

For example, a measurement point is designated for the first image. The measurement processing unit 44 processes a video signal, thereby retrieving a corresponding point of the second image that corresponds to the measurement point of the first image. In other words, the measurement processing unit 44 retrieves a corresponding point through pattern matching between the first image and the second image. The measurement processing unit 44 calculates three-dimensional coordinates corresponding to the measurement point on the basis of the principle of triangulation using the measurement point and the corresponding point.

In the stereo measurement, the first optical image and the second optical image are formed in the imaging element 28 simultaneously or alternately. For example, in a case in which the first optical image and the second optical image are alternately formed in the imaging element 28, one of a first optical path and a second optical path is shielded by a movable mechanical shutter. The first optical path is an optical path used for forming the first optical image. The second optical path is an optical path used for forming the second optical image. In a case in which the mechanical shutter is disposed in the second optical path, the first optical image is formed in the imaging element 28. In a case in which the mechanical shutter is disposed in the first optical path, the second optical image is formed in the imaging element 28.

In the stereo measurement, by projecting a pattern onto a subject, the accuracy of the matching process is improved. For this reason, in the stereo measurement, a pattern may be projected on a subject. The measurement processing unit 44 may execute a process of three-dimensional measurement other than the stereo measurement. For example, the measurement processing unit 44 may execute a measurement process based on the principle of a phase shift method.

As shown in FIG. 3, the illumination unit 29 includes a plurality of independent light sources (the LED 29a and the LED 29b). The illumination control unit 46 selects the light source that will generate illumination light in accordance with the set operation mode.

The illumination unit 29 includes a plurality of light sources (the LED 29a and the LED 29b) including a measurement light source (the LED 29b) used for projecting a pattern or stripes on a subject. The endoscope apparatus 1 includes a measurement processing unit 44 that executes a measurement process on the basis of a video signal. The plurality of operation modes includes an operation mode in which at least the measurement process is executed. In a case in which the operation mode in which at least the measurement process is executed is set, the illumination control unit 46 may turn on the measurement light source.

For example, in a case in which an observation mode M1 is set, the illumination control unit 46 selects the LED 29a. On the other hand, in a case in which an observation/measurement mode M2 or a measurement mode M3 is set in the endoscope apparatus 1, and general stereo measurement is executed, the illumination control unit 46 selects the LED 29a. In a case in which the measurement mode M3 is set in the endoscope apparatus 1, and a pattern or stripes are projected onto a subject, the illumination control unit 46 selects the LED 29b.

Figure 7:
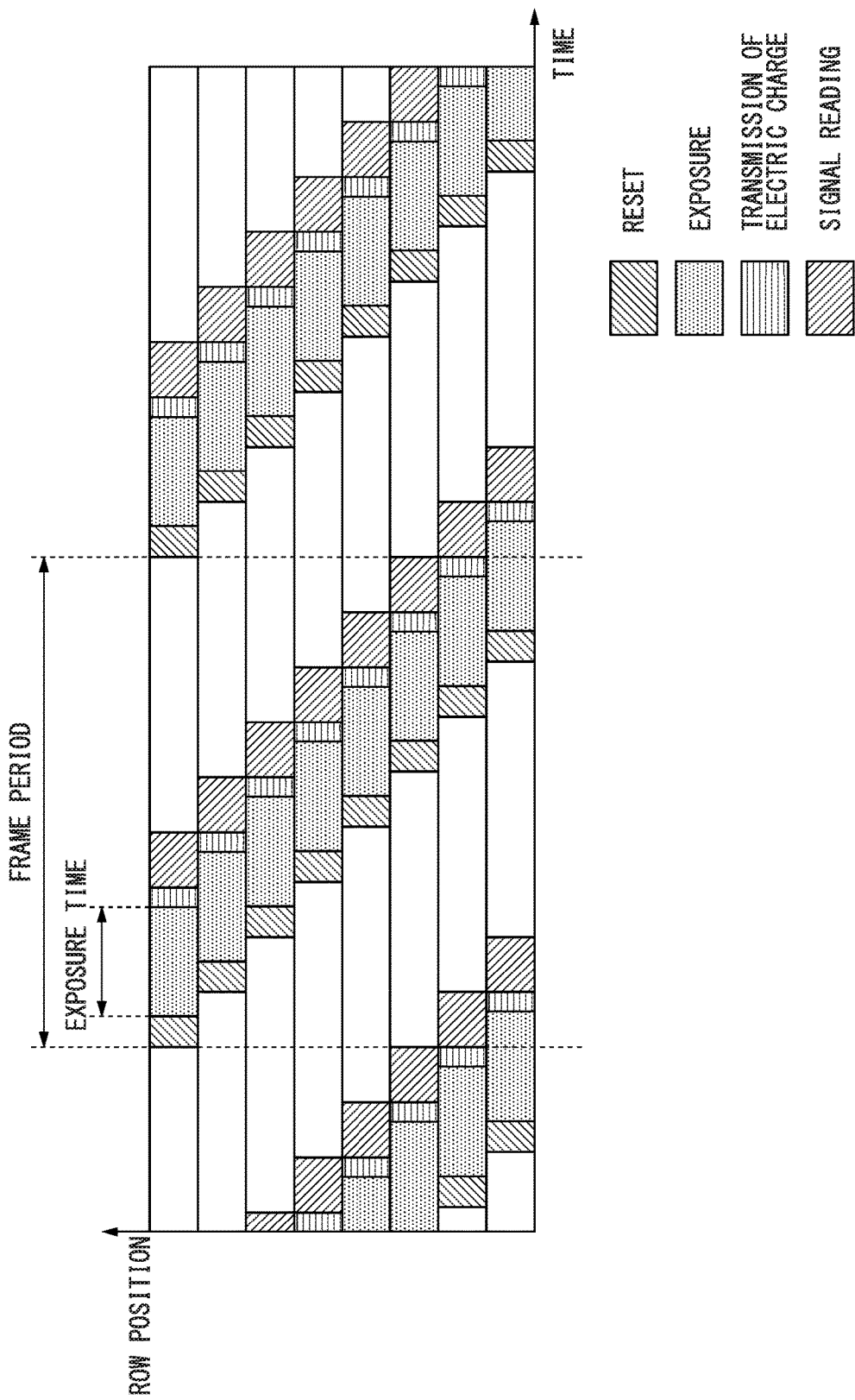
FIG. 7 is a timing chart showing the operation of the endoscope apparatus according to an embodiment of the present invention.

The operation of the endoscope apparatus 1 will be described. FIG. 7 shows an operation executed in a case in which the imaging element 28 is driven by a rolling shutter. In FIG. 7, the horizontal direction represents the time, and the vertical direction represents the row position. FIG. 7 shows an operation of pixels 54 of eight rows. The uppermost row is the first row, and the lowermost row is the eighth row. For example, in the operation shown in FIG. 7, the light source of the illumination unit 29 is continuously controlled to be turned on.

When a frame period based on a display period of the monitor 4 starts, resetting is executed in the pixel 54 of the first row. In other words, in the pixels 54 of the first row, the resetting unit 63 resets electric charge in the photoelectric conversion unit 60 and the electric charge accumulating unit 62. Accordingly, exposure starts in the pixels 54 of the first row. After resetting, transmission of electric charge is executed in the pixels 54 of the first row. In other words, in the pixels 54 of the first row, the electric charge transmitting unit 61 transmits electric charge generated by the photoelectric conversion unit 60 to the electric charge accumulating unit 62. In this way, the exposure in the pixels 54 of the first row ends. A period from exposure start to exposure end is an exposure period (exposure possible period). In other words, the exposure period is a period from the end of resetting to the start of transmission of electric charge. After the transmission of electric charge, signal reading is executed in the pixels 54 of the first row. In other words, in the pixels 54 of the first row, the output unit 65 outputs an imaging signal to the vertical signal line 56. After signal reading is executed, the pixels 54 of the first row wait until the next frame period starts.

At a timing at which a predetermined time elapses from a timing at which resetting is executed in the pixels 54 of the first row, resetting is executed in the pixels 54 of the second row. An operation executed in the pixels 54 of the second row is similar to that executed in the pixels 54 of the first row. The operation in the pixels 54 of the second row is executed at a timing shifted from the timing of the operation executed in the pixels 54 of the first row by a predetermined time. Similarly, an operation in the pixels 54 of each of rows that are the third row and subsequent rows is executed at a timing shifted from the timing of the operation executed in the pixels 54 of the previous row by a predetermined time.

Figure 8:
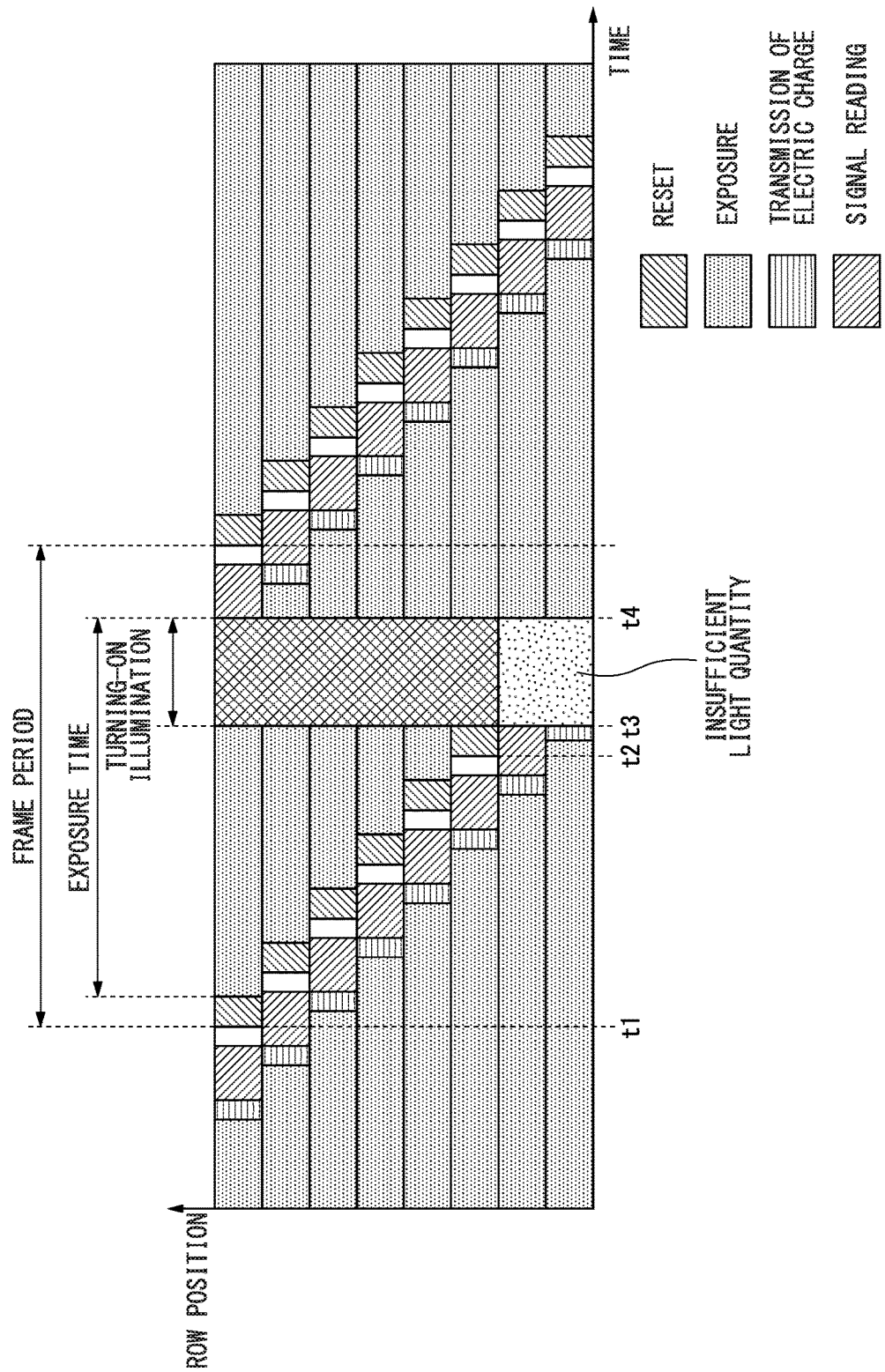
FIG. 8 is a timing chart showing the operation of an endoscope apparatus according to an embodiment of the present invention.

FIG. 8 shows a featured operation of the endoscope apparatus 1. In FIG. 8, the horizontal direction represents the time, and the vertical direction represents the row position. FIG. 8 shows an operation of pixels 54 of eight rows. The uppermost row is the first row, and the lowermost row is the eighth row.

In the operation shown in FIG. 8, the imaging element 28 is driven by a rolling shutter. Exposure periods are set such that at least parts of the exposure periods of the pixels 54 of two or more rows overlap each other. In the operation shown in FIG. 8, exposure periods are set such that at least parts of the exposure periods of the pixels 54 of the first row to the eighth row overlap each other. The illumination control unit 46 controls the illumination unit 29 such that the light source of the illumination unit 29 is intermittently turned on.

At a timing t1 at which resetting starts in the pixels 54 of the first row, the light source of the illumination unit 29 is turned off. At a timing t3 at which signal reading in the pixels 54 of the sixth row ends, the light source of the illumination unit 29 becomes turned on. For example, a timing t2 at which imaging signals of the pixels 54 of the sixth row are output is notified from the video signal generating unit 41 to the illumination control unit 46. The illumination control unit 46 calculates the timing t3 on the basis of the timing t2. The illumination control unit 46 turns on the light source of the illumination unit 29 at the calculated timing t3. At a timing t4 at which signal reading starts in the pixels 54 of the first row, the light source of the illumination unit 29 becomes turned off. For example, the illumination control unit 46 calculates the timing t4 on the basis of the timing t3. The illumination control unit 46 turns off the light source of the illumination unit 29 at the calculated timing t4.

As described above, in the period from the timing t3 to the timing t4 during which the pixels 54 of the first row to the sixth row are simultaneously exposed, the light source of the illumination unit 29 is turned on. In a case in which the surroundings of the tip end part 21 are dark, most of light incident to the plurality of pixels 54 is based on the light of only light sources of the illumination unit 29 that are turned on from the timing t3 to the timing t4. For this reason, in the pixels 54 of the first row to the sixth row of the imaging element 28 driven by a rolling shutter, a subject image based on light that is simultaneously incident to the pixels 54 is captured. Accordingly, in the image based on the imaging signals output from the pixels 54 from the first row to the sixth row, distortion of the subject is decreased.

A period other than the exposure period in the pixels 54 of the seventh row and the eighth row is included in a period from the timing t3 to the timing t4. In other words, a length of a period in which the pixels 54 of the seventh row and the eighth row are exposed is shorter than a length of a period in which the pixels 54 of the first row to the sixth row are exposed. For this reason, in the pixels 54 of the seventh row and the eighth row, compared to the pixels 54 of the first row to the sixth row, the exposure amount is insufficient.

The control unit 47 controls at least one of a scanning rate, a scanning area, a scanning start timing, an exposure time, and a gain in accordance with a set operation mode.

The scanning rate is a scanning speed of the plurality of pixels 54. A difference in the operation timings of pixels 54 of each row disposed in the imaging element 28 driven by a rolling shutter is based on the scanning rate. An imaging signal is read from the pixels 54 of each row at a timing based on the scanning rate.

The scanning area includes all or some of the plurality of pixels 54 disposed in the imaging area of the imaging element 28. The scanning area includes all of the pixels 54 in which at least resetting and transmission of electric charge are executed and includes at least all of the pixels 54 in which signal reading is executed. The scanning area may include pixels 54 in which resetting and transmission of electric charge are executed, and signal reading is not executed. In the scanning area, all of the rows include one or more pixels 54 from which imaging signals are read. Imaging signals are read from all or some of the pixels 54 disposed in the scanning area. For example, block reading in which imaging signals are read only from pixels 54 disposed in parts of all of the columns may be executed. The control unit 47 may control an area in which block reading is executed in the scanning area.

In the operation shown in FIG. 8, the pixels 54 of the first row to the eighth row are included in the scanning area. In a case in which the light source of the illumination unit 29 is turned on from the timing t3 to the timing t4, only the pixels 54 of the first row to the sixth row may be included in the scanning area. The control unit 47 controls the imaging element 28 such that imaging signals are output only from the pixels 54 of the scanning area. In a case in which the scanning area is set only in a part of the imaging area, the processing load of the CPU 18 required for reading imaging signals is decreased. In a case in which the observation/measurement mode M2 is set, the endoscope apparatus 1 can execute generation of imaging signals and the measurement process in one frame period. In other words, the endoscope apparatus 1 can executes the measurement process in real time in synchronization with continuous imaging operations.

A scanning start timing is a timing at which the scanning of the plurality of pixels 54 starts. The scanning start timing represents a start timing of the operations of the plurality of pixels 54 in the frame period. In a case in which the pixels 54 of the rows are sequentially scanned from the pixels 54 of the first row, the scanning start timing represents a start timing of the operations of the pixels 54 of the first row. For example, the scanning start timing represents a timing at which resetting starts in the pixels 54 of the first row.

An exposure time is the length of the exposure period. In other words, the exposure time is time from the timing of the end of resetting to the timing of the start of transmission of electric charge. The exposure time in the operation shown in FIG. 7 may be longer than the exposure time in the operation shown in FIG. 6. As the exposure time is increased, the exposure periods of the pixels 54 of more rows can easily overlap each other.

A gain is a gain of amplification in the video signal generating unit 41 or the signal processing unit 52. A different gain may be set for each row of the arrangement of the plurality of pixels 54.

The illumination control unit 46 controls at least one of a turning-on timing, a turning-on time, and a light quantity of the light source in accordance with a set operation mode.

A turning-on timing is a timing at which the light source of the illumination unit 29 starts to be turned on. A turning-on time is time in which the light source of the illumination unit 29 continues to be turned on. In other words, the turning-on time is time from a turning-on start timing (turning-on timing) to a turning-on end timing (turning-off timing). In a case in which the light source of the illumination unit 29 is intermittently turned on, the turning-on time is shorter than the exposure time. A light quantity is the light quantity of the light source of the illumination unit 29. In the operation shown in FIG. 7, the illumination control unit 46 controls the illumination unit 29 such that the light source of the illumination unit 29 is turned on in a period in which at least parts of the exposure periods of the pixels 54 of the first row to the eighth row included in the scanning area overlap each other.

In a case in which an operation mode in which at least the measurement process is executed is set, the control unit 47 may control the imaging element 28 such that at least parts of the exposure periods of pixels 54 disposed in at least a part of the scanning area overlap each other. In a case in which an operation mode in which at least the measurement process is executed is set, the illumination control unit 46 may control the illumination unit 29 such that the light source is turned on in a period in which at least parts of the exposure periods of pixels 54 disposed in at least a part of the scanning area overlap each other. In this way, the endoscope apparatus 1 can execute the measurement process on the basis of an image in which the distortion of the subject is decreased. In other words, the measurement accuracy is improved.

Figure 9:
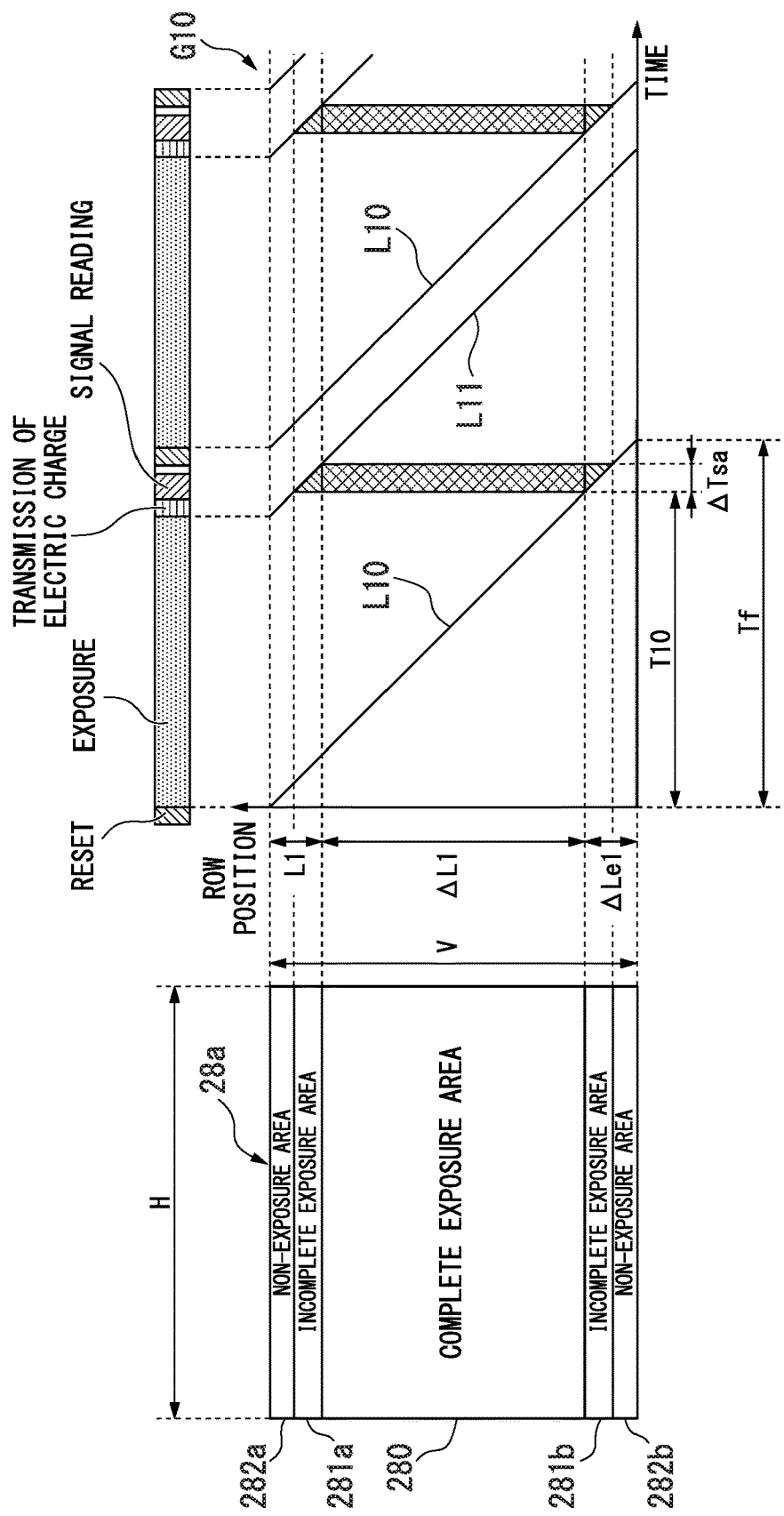
FIG. 9 is a timing chart showing the operation of an endoscope apparatus according to an embodiment of the present invention.
Figure 10:
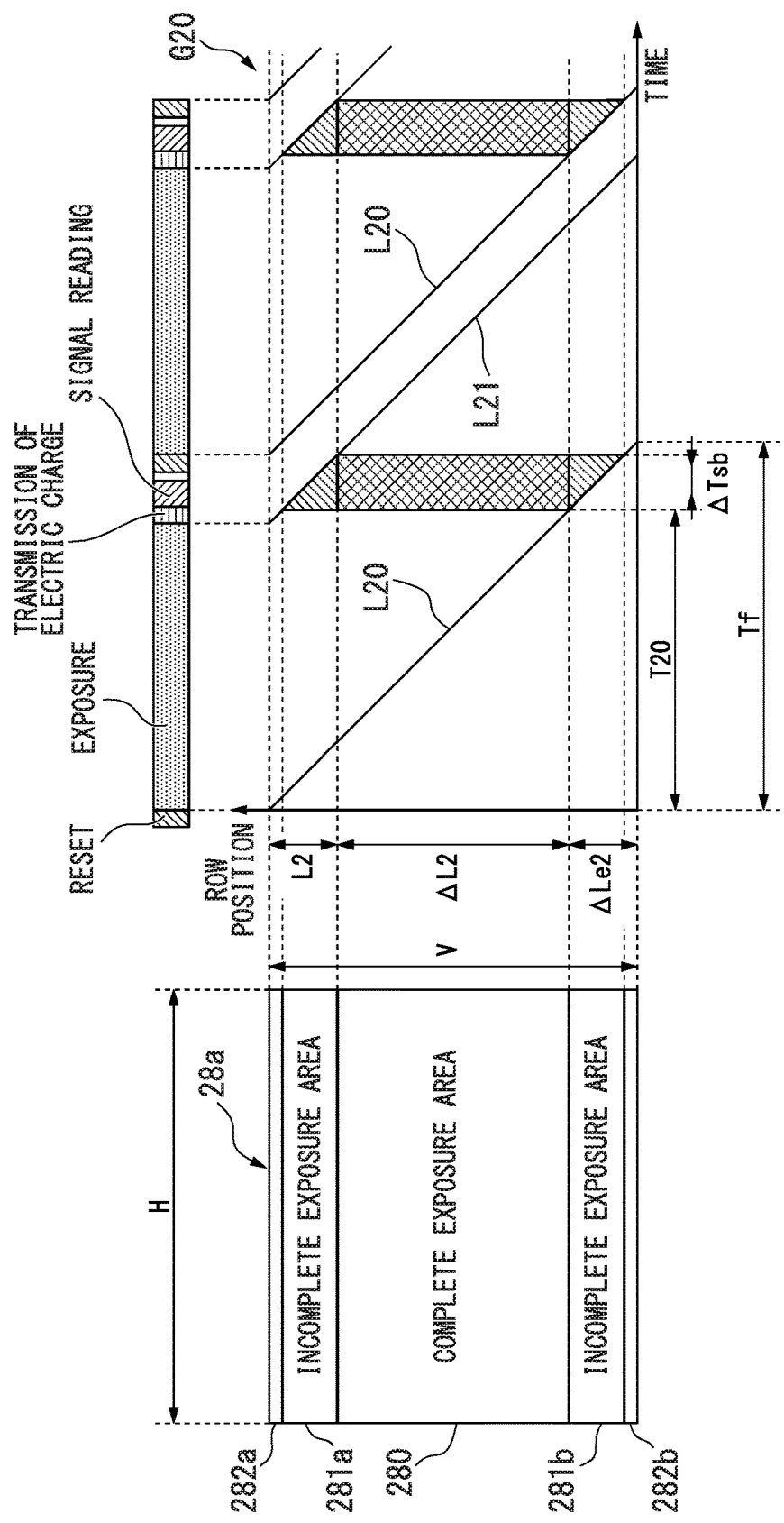
FIG. 10 is a timing chart showing the operation of an endoscope apparatus according to an embodiment of the present invention.

FIGS. 9 and 10 show a difference between lengths of periods in which light is emitted to each pixel 54 by turning-on the light source of the illumination unit 29. A plurality of pixels 54 are disposed in an imaging area 28a. The number of horizontal pixels of the imaging area 28a, in other words, the number of columns is H. The number of vertical pixels of the imaging area 28a, in other words, the number of rows is V. The imaging area 28a is divided into a plurality of areas in accordance with a length of a period in which light is emitted in an exposure period. As shown in FIGS. 9 and 10, the imaging area 28a is divided into a complete exposure area 280, an incomplete exposure area 281a, an incomplete exposure area 281b, a non-exposure area 282a, and a non-exposure area 282b.

The incomplete exposure area 281a and the incomplete exposure area 281b are adjacent to the complete exposure area 280. The incomplete exposure area 281a is disposed on the upper side of the complete exposure area 280. The incomplete exposure area 281b is disposed on the lower side of the complete exposure area 280. The non-exposure area 282a is adjacent to the incomplete exposure area 281a, and the non-exposure area 282b is adjacent to the incomplete exposure area 281b. The non-exposure area 282a is disposed on the upper side of the incomplete exposure area 281a. The non-exposure area 282b is disposed on the lower side of the incomplete exposure area 281b.

In FIGS. 9 and 10, a graph G10 and a graph G20 represent timings of the operation of each pixel 54 of the imaging area 28a. In the graphs G10 and G20, the horizontal direction represents the time, and the vertical direction represents the row position. The uppermost row is the first row, and the lowermost row is the V-th row. On the upper side of the graphs G10 and G20, the timings of the operation of the pixels 54 disposed in the first row is schematically shown. The operations of the pixel 54 include resetting, transmission of electric charge, and signal reading. In FIGS. 9 and 10, operations of a case in which the entire imaging area 28a is set as the scanning area are shown.

Each of a straight line L10 and a straight line L20 represents an end timing of resetting, in other words, a start timing of exposure in the pixels 54 of each row disposed in the imaging area 28a. Each of a straight line L11 and a straight line L21 represents a start timing of transmission of electric charge in the pixels 54 of each row disposed in the imaging area 28a, in other words, an end timing of exposure. The slope of the straight line L10, the straight line L11, the straight line L20, and the straight line L21 is based on the scanning rate. In the operation represented in the graph G10, an exposure period is a period from a timing represented by the straight line L10 to a timing represented by the straight line L11. Similarly, in the operation represented in the graph G20, an exposure period is a period from a timing represented by the straight line L20 to a timing represented by the straight line L21. The length of the frame period, in other words, the display period of the monitor 4 is Tf. A frame rate for displaying a live image is 1/Tf1.

In the operation represented in the graph G10, the turning-on of the light source of the illumination unit 29 starts at a timing at which time T10 has elapsed from the start timing of the exposure of the pixels 54 of the first row represented in the straight line L10. In other words, the timing at which the time T10 has elapsed from the start timing of the exposure of the pixels 54 of the first row is a turning-on timing. The time T10 may be arbitrarily set. A timing at which imaging signals of the pixels 54 of the first row are output is notified from the video signal generating unit 41 to the illumination control unit 46. The illumination control unit 46 calculates a turning-on timing on the basis of the notified timing. The illumination control unit 46 turns on the light source of the illumination unit 29 at the calculated turning-on timing.

At a timing at which time ΔTsa has elapsed from the turning-on timing, the turning-on of the light source of the illumination unit 29 ends. In other words, a timing at which the time ΔTsa has elapsed from the turning-on timing is turning-off timing. The time ΔTsa may be arbitrarily set. The illumination control unit 46 calculates a turning-off timing on the basis of the turning-on timing. The illumination control unit 46 turns off the light source of the illumination unit 29 at the calculated turning-off timing.

In the operation represented in the graph G10, in a period in which the light source of the illumination unit 29 is intermittently turned on, at least parts of exposure periods of the pixels 54 of the incomplete exposure area 281*a*, the complete exposure area 280, and the incomplete exposure area 281*b* overlap each other.

The operation described above is executed in the frame period. The operation described above may be repeatedly executed in a plurality of frame periods. In the operations represented in the graph G10 and the graph G20, the same operation is repeatedly executed in a plurality of frame periods.

In the imaging area 28*a*, in the pixels 54 of rows other than a row L1 disposed on the upper side and a row ΔLe1 disposed on the lower side, the turning-on timing and the turning-off timing are included in the exposure period. In such pixels 54, periods in which light is incident to the pixels 54 in accordance with the tuning-on of the light source of the illumination unit 29 in the exposure period are the same. Such pixels 54 constitute the complete exposure area 280. In FIG. 9, the number of rows of the complete exposure area 280 is ΔL1.

In the incomplete exposure area 281*a* and the incomplete exposure area 281*b*, only a part of the turning-on time is included in the exposure period. In the incomplete exposure area 281*a*, the turning-on timings are the same, and the end timings of exposure are different from each other in accordance with the row position of the pixel 54. For this reason, in the incomplete exposure area 281*a*, a length of a period in which light is incident to the pixel 54 in accordance with the turning-on of the light source of the illumination unit 29 in the exposure period is different in accordance with the row position of the pixel 54. In the incomplete exposure area 281*b*, the start timings of exposure are different from each other in accordance with the row position of the pixel 54, and the turning-off timings are the same. For this reason, in the incomplete exposure area 281*b*, a length of a period in which light is incident to the pixel 54 in accordance with the turning-on of the light source of the illumination unit 29 in the exposure period is different in accordance with the row position of the pixel 54.

After the exposure in the pixels 54 of the non-exposure area 282*a* ends, the light source of the illumination unit 29 is turned on. For this reason, in the non-exposure area 282*a*, an imaging signal based on electric charge accumulated in the photoelectric conversion unit 60 in accordance with the turning-on of the light source is not acquired. After the light source of the illumination unit 29 is turned off, exposure in the pixels 54 of the non-exposure area 282*b* starts. For this reason, in the non-exposure area 282*b*, an imaging signal based on electric charge accumulated in the photoelectric conversion unit 60 in accordance with the turning-on of the light source is not acquired.

In the operation represented in the graph G20, at a timing at which time T20 has elapsed from the start timing of exposure in the pixels 54 of the first row represented by the straight line L20, the turning-on of the light of the illumination unit 29 starts. In other words, the timing at which the time T20 has elapsed from the start timing of exposure in the pixels 54 disposed in the first row is a turning-on timing. The time T20 is different from the time T10.

At a timing at which time ΔTsb has elapsed from the turning-on timing, the turning-on of the light source of the illumination unit 29 ends. In other words, a timing at which the time ΔTsb has elapsed from the turning-on timing is a turning-off timing. The time ΔTsb is different from the time ΔTsa. Since the time T10 and the time T20 are different and the time ΔTsa and the time ΔTsb are different, the turning-on times are different.

In an operation represented in the graph G20, in a period in which the light source of the illumination unit 29 is intermittently turned on, at least parts of the exposure periods of the pixels 54 of the incomplete exposure area 281*a*, the complete exposure area 280, and the incomplete exposure area 281*b* overlap each other.

In the imaging area 28*a*, pixels 54 of rows other than a row L2 disposed on the upper side and a row ΔLe2 disposed on the lower side constitute the complete exposure area 280. In the case shown in FIG. 10, the number of rows of the complete exposure area 280 is ΔL2.

In the cases shown in FIGS. 9 and 10, the numbers of rows of the complete exposure areas 280 are different from each other. Similarly, in the cases shown in FIGS. 9 and 10, the numbers of rows of the incomplete exposure areas 281*a* are different, and the numbers of rows of the incomplete exposure areas 281*b* are different. Similarly, in the cases shown in FIGS. 9 and 10, the numbers of rows of the non-exposure areas 282*a* are different, and the numbers of rows of the non-exposure areas 282*b* are different. As described above, the number of rows of the complete exposure area 280 and the like are different in accordance with a turning-on timing and a turning-on time. In other words, the endoscope apparatus 1 can control the sizes and the row positions of the complete exposure area 280 and the like by controlling a turning-on timing and a turning-on time.

For example, the complete exposure area 280 may include only pixels 54 of an effective pixel area of the imaging element 28. The complete exposure area 280 may include only pixels 54 corresponding to an area of an image displayed in the monitor 4. The complete exposure area 280 may include only pixels 54 of an area used for the measurement process. The scanning area may include only pixels 54 of the complete exposure area 280. The scanning area may include only pixels 54 of the complete exposure area 280, the incomplete exposure area 281*a*, and the incomplete exposure area 281*b*.

The illumination control unit 46 may control the illumination unit 29 such that the light source of the illumination unit 29 is turned on in a period in which at least parts of exposure periods of all of the pixels 54 disposed in the scanning area overlap each other, and such that lengths of periods in which illumination light is emitted to a subject during the exposure period are the same in all of the pixels 54 disposed in the scanning area. In such a case, all of the pixels 54 disposed in the scanning area are included in the complete exposure area 280.

The illumination control unit 46 may control the turning-on timing and the turning-on time such that a center row position of the complete exposure area 280 is fixed. In a case in which such control is executed, the scanning area may include only the pixels 54 of the complete exposure area 280. Since the center row position of the complete exposure area 280 is fixed regardless of the number of rows of the complete exposure area 280, a change in the position of a subject in an image that is based on imaging signals acquired from the complete exposure area 280 is suppressed.

A method of driving the imaging element 28 is a rolling shutter. The video signal generating unit 41 may generate video signals by amplifying imaging signals with a predetermined gain. The scanning area may include a first area and a second area. The first area is an area in which a length of a period, in which illumination light is emitted to a subject in the exposure period, is a first time. The second area is an area in which a length of a period, in which illumination light is emitted to a subject in the exposure period, is a second time that is shorter than the first time. A second gain may have a value calculated by dividing the first time by the second time and multiplying a quotient thereof by a first gain. The second gain is a gain used when imaging signals read from pixels 54 disposed in the second area are amplified by the video signal generating unit 41. The first gain is a gain used when imaging signals read from pixels 54 disposed in the first area are amplified by the video signal generating unit 41.

The imaging element 28 includes a signal processing unit 52 (signal processing circuit) that amplifies imaging signals output from a plurality of pixels 54 with a predetermined gain. The second gain may be a value calculated by dividing the first time by the second time and multiplying a quotient thereof by the first gain. The second gain is a gain used when imaging signals read from pixels 54 disposed in the second area are amplified by the signal processing unit 52. The first gain is a gain used when imaging signals read from pixels 54 disposed in the first area are amplified by the signal processing unit 52.

In the cases shown in FIGS. 9 and 10, the first area is the complete exposure area 280, and the second area is the incomplete exposure area 281a and the incomplete exposure area 281b. The control unit 47 calculates the second gain by dividing the first time by the second time and multiplying a quotient thereof by the first gain. In this way, the second gain is set to a value larger than that of the first gain. As a result, a length of a period in which light is incident to the pixels 54 of the second area and a length of a period in which light is incident to the pixels 54 of the first area are substantially the same. In other words, the insufficiency of the exposure amount in the second area is remedied.

Equation (1) to Equation (3) represent gains G(l) regarding imaging signals of the pixels 54 of the l-th row.

$$G(l) = \alpha(l) \cdot G0 \quad (l \leq Lt) \tag{1}$$

$$G(l) = G0 \quad (Lt < l \leq Lt + \Delta Lt) \tag{2}$$

$$G(l) = \alpha(l) \cdot G0 \quad (Lt + \Delta Lt < l) \tag{3}$$

In the equations described above, l is the row position of each of the pixels 54 of the complete exposure area 280, the incomplete exposure area 281a, and the incomplete exposure area 281b. Equation (1) represents a gain regarding imaging signals of the pixels 54 of the incomplete exposure area 281a that is the second area. Equation (2) represents a gain regarding imaging signals of the pixels 54 of the complete exposure area 280 that is the first area. Equation (3) represents a gain regarding imaging signals of the pixels 54 of the incomplete exposure area 281b that is the second area. G0 is a predetermined value. Lt is the position of a row closest to the complete exposure area 280 in the incomplete exposure area 281a. ΔLt is the number of rows of the complete exposure area 280.

α(l) is a value acquired by dividing the first time by the second time. The second time has a value for the row position of the pixel 54 in the incomplete exposure area 281a or the incomplete exposure area 281b. Equation (4) represents a value acquired by dividing the first time ΔTs1 by the second time ΔTs2 for the pixel 54 of the incomplete exposure area 281a. Equation (5) represents a value acquired by dividing the first time ΔTs1 by the second time ΔTs2 for the pixel 54 of the incomplete exposure area 281b.

$$\Delta Ts1/Ts2 = Lt1/(la - lt + 1) \tag{4}$$

$$\Delta Ts1/Ts2 = Lt2/(lb - la + 1) \tag{5}$$

In the equations described above, la is a row position of the pixel 54 of the incomplete exposure area 281a or the incomplete exposure area 281b. lt is the uppermost row position in the incomplete exposure area 281a. lb is the lowermost row position in the incomplete exposure area 281b. Lt1 is the number of rows of the incomplete exposure area 281a. Lt2 is the number of rows of the incomplete exposure area 281b.

The control unit 47 calculates a gain G(l) for the row position of each of the pixels 54 of the complete exposure area 280, the incomplete exposure area 281a, and the incomplete exposure area 281b. The control unit 47 outputs a control signal used for setting the gain G(l). On the basis of this control signal, the gain G(l) is set in the video signal generating unit 41 or the signal processing unit 52.

Figure 11:
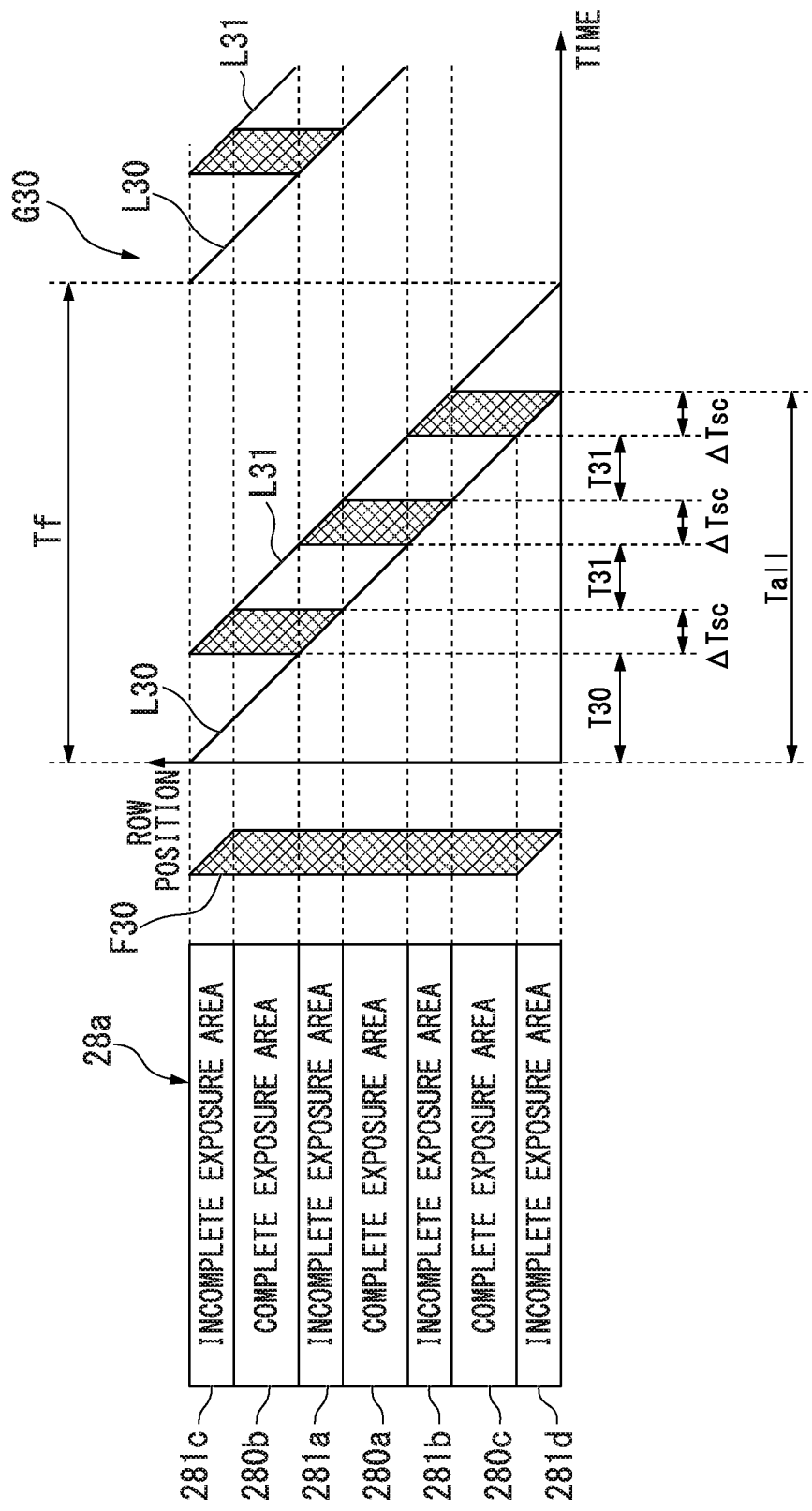
FIG. 11 is a timing chart showing the operation of an endoscope apparatus according to an embodiment of the present invention.

FIG. 11 shows an operation of an endoscope apparatus 1 that is different from the operations shown in FIGS. 8 to 10. In the operation shown in FIG. 11, the light source of the illumination unit 29 is turned on plural times in a frame period. An imaging area 28a is divided into a plurality of areas. As shown in FIG. 11, the imaging area 28a is divided into a complete exposure area 280a, a complete exposure area 280b, a complete exposure area 280c, an incomplete exposure area 281a, an incomplete exposure area 281b, an incomplete exposure area 281c, and an incomplete exposure area 281d.

In the imaging area 28a, a complete exposure area and an incomplete exposure area are alternately disposed in the vertical direction. The upper end of the imaging area 28a is the incomplete exposure area 281c, and the lower end of the imaging area 28a is the incomplete exposure area 281d. Between the incomplete exposure area 281c and the incomplete exposure area 281d, the complete exposure area 280b, the incomplete exposure area 281a, the complete exposure area 280a, the incomplete exposure area 281b, and the complete exposure area 280c are sequentially disposed from the top.

In FIG. 11, a graph G30 shows the timing of the operation of each pixel 54 in the imaging area 28a. In the graph G30, the horizontal direction represents the time, and the vertical direction represents the row position. The uppermost row is the first row, and the lowermost row is the V-th row. In FIG. 11, an operation of a case in which the entire imaging area 28a is set as the scanning area is shown.

A straight line L30 represents an end timing of resetting, in other words, a start timing of exposure in the pixels 54 of each row disposed in the imaging area 28a. A straight line L31 represents a start timing of transmission of electric charge, in other words, an end timing of exposure in the pixels 54 of each row disposed in the imaging area 28a. The slope of the straight line L30 and the straight line L31 is based on the scanning rate. An exposure period is a period from a timing represented by the straight line L30 to a timing represented by the straight line L31. The length of the frame period, in other words, the display period of the monitor 4 is Tf. A frame rate for displaying a live image is 1/Tf.

In the operation shown in the graph G30, the light source of the illumination unit 29 is turned on three times in one frame period. In other words, the light source of the illumination unit 29 starts turning-on at a first timing, a second timing, and a third timing in one frame period. At a timing at which time T30 has elapsed from the start timing of exposure in the pixels 54 of the first row represented by a straight line L30, the turning-on of the light source of the illumination unit 29 starts. In other words, a timing at which the time T30 has elapsed from the start timing of exposure in the pixels 54 of the first row is the first turning-on timing. The first turning-on timing is the same as start timing of the transmission of electric charge in the pixels 54 of the first row represented by a straight line L31. Thus, the time T30 that is a difference between the start timing of exposure in the pixels 54 of the first row and the first turning-on timing is the same as an exposure time. A timing at which imaging signals of the pixels 54 of the first row is notified from the video signal generating unit 41 to the illumination control unit 46. The illumination control unit 46 calculates the first turning-on timing on the basis of the notified timing. The illumination control unit 46 turns on the light source of the illumination unit 29 at the calculated first turning-on timing.

At a timing at which time ΔTsc has elapsed from the first turning-on timing, the turning-on of the light source of the illumination unit 29 ends. In other words, a timing at which the time ΔTsc has elapsed from the first turning-on timing is a first turning-off timing. The time ΔTsc may be arbitrarily set. The illumination control unit 46 calculates the first turning-off tinting on the basis of the first turning-on timing. The illumination control unit 46 turns off the light source of the illumination unit 29 at the calculated first turning-off timing.

At a timing at which time T31 has elapsed from the first turning-off timing, the turning-on of the light source of the illumination unit 29 starts. In other words, a timing at which the time T31 has elapsed from the first turning-off timing is a second turning-on timing. The first turning-on timing is an end timing of resetting of pixels 54 of a predetermined row. The second turning-on timing is a start timing of transmission of electric charge in the pixels 54 of the row. Thus, a length of a period that is a difference between the first turning-on timing and the second turning-on timing is the same as an exposure time. The illumination control unit 46 calculates the second turning-on timing on the basis of the first turning-on timing. The illumination control unit 46 turns on the light source of the illumination unit 29 at the calculated second turning-on timing.

As described above, the illumination control unit 46 turns on the light source of the illumination unit 29 at the first tuning-on timing that is a start timing of exposure of pixels 54 of a predetermined row. The illumination control unit 46 turns on the light source of the illumination unit 29 at the second turning-on timing at which the exposure time has elapsed from the first turning-on timing after the light source of the illumination unit 29 is turned off at the first turning-off timing.

The turning-on of the light source of the illumination unit 29 ends at a timing at which time ΔTsc has elapsed from the second turning-on timing. In other words, a timing at which the time ΔTsc has elapsed from the second turning-on timing is the second turning-off timing. The illumination control unit 46 calculates the second turning-off timing on the basis of the second turning-on timing. The illumination control unit 46 turns off the light source of the illumination unit 29 at the calculated second turning-off timing.

The turning-on of the light source of the illumination unit 29 starts at a timing at which time T31 has elapsed from the second turning-off timing. In other words, a timing at which the time T31 has elapsed from the second turning-off timing is the third turning-on timing. The second turning-on timing is an end timing of resetting of pixels 54 of a predetermined row. The third turning-on timing is a start timing of transmission of electric charge in the pixels 54 of the row. Thus, a length of a period that is a difference between the second turning-on timing and the third turning-on timing is the same as an exposure time. The illumination control unit 46 calculates the third turning-on timing on the basis of the second turning-on timing. The illumination control unit 46 turns on the light source of the illumination unit 29 at the calculated third turning-on timing.

As described above, the illumination control unit 46 turns on the light source of the illumination unit 29 at the second tuning-on timing that is a start timing of exposure of pixels 54 of a predetermined row. The illumination control unit 46 turns on the light source of the illumination unit 29 at the third turning-on timing at which the exposure time has elapsed from the second turning-on timing after the light source of the illumination unit 29 is turned off at the second turning-off timing.

The turning-on of the light source of the illumination unit 29 ends at a timing at which time ΔTsc has elapsed from the third turning-on timing. In other words, a timing at which the time ΔTsc has elapsed from the third turning-on timing is the third turning-off timing. The illumination control unit 46 calculates the third turning-off timing on the basis of the third turning-on timing. The illumination control unit 46 turns off the light source of the illumination unit 29 at the calculated third turning-off timing.

In an operation represented in the graph G30, the light source of the illumination unit 29 is intermittently turned on three times in a period from a timing at which resetting of the pixels 54 of the first row starts (scan start timing) to a timing at which signal reading in the pixels 54 of the V-th row is ended (scan end timing). In the turning-on period of the first time of the light source of the illumination unit 29, at least parts of the exposure periods of the pixels 54 of the incomplete exposure area 281c, the complete exposure area 280b, and the incomplete exposure area 281a overlap each other. In the turning-on period of the second time of the light source of the illumination unit 29, at least parts of the exposure periods of the pixels 54 of the incomplete exposure area 281a, the complete exposure area 280a, and the incomplete exposure area 281b overlap each other. In the turning-on period of the third time of the light source of the illumination unit 29, at least parts of the exposure periods of the pixels 54 of the incomplete exposure area 281b, the complete exposure area 280c, and the incomplete exposure area 281d overlap each other.

The operation described above is executed in the frame period. The operation described above may be repeatedly executed in a plurality of frame periods. In the operation represented in the graph G30, the same operation is repeatedly executed in a plurality of frame periods.

In a case in which the entire imaging area 28a is the scanning area, and the exposure period cannot be set such that at least parts of exposure periods of all of the pixels 54 disposed in the scanning area overlap each other, the operation represented in the graph G30 is executed. In this way, the endoscope apparatus 1 can acquire imaging signals of all of the pixels 54 disposed in the scanning area.

In the operation represented in the graph G30, the first turning-on timing is a start timing of transmission of electric charge in the pixels 54 of the first row, and the third turning-off timing is an end timing of resetting in the pixels 54 of the V-th row. In this way, all of the pixels 54 disposed in the imaging area 28a are included in a complete exposure area or an incomplete exposure area. Equation (6) represents time Tall from an end timing of resetting in the pixels 54 of the first row to an end timing of resetting in the pixels 54 of the V-th row.

$$Tall = T30 + 2 \times T31 + 3 \times \Delta Tsc \qquad (6)$$

The time T30 is the same as the exposure time. A sum of the time ΔTsc and the time T31 is the same as the exposure time. In a case in which the time Tall is given, the illumination control unit 46 determines the time ΔTsc and the time T31 to satisfy Equation (6).

A length of a period in which light is incident to pixels 54 by turning-on the light source of the illumination unit 29 in the exposure period is the same among the complete exposure area 280*a*, the complete exposure area 280*b*, and the complete exposure area 280*c*. Only a part of turning-on time is included in the exposure period in the incomplete exposure area 281*a*, the incomplete exposure area 281*b*, the incomplete exposure area 281*c*, and the incomplete exposure area 281*d*. A length of a period in which light is incident to the pixel 54 by turning-on the light source of the illumination unit 29 in the exposure period is different in accordance with the row position of the pixel 54 in the incomplete exposure area 281*c* and the incomplete exposure area 281*d*. A length of a period in which light is incident to the pixel 54 by turning-on the light source of the illumination unit 29 once in the exposure period is different in accordance with the row position of the pixel 54 in the incomplete exposure area 281*a* and the incomplete exposure area 281*b*. However, the light source of the illumination unit 29 is turned on twice in the incomplete exposure area 281*a* and the incomplete exposure area 281*b* in the exposure period. A sum of time in which light is incident to pixels 54 by turning-on the light source of the illumination unit 29 twice in the exposure period is the same in the incomplete exposure area 281*a* and the incomplete exposure area 281*b*.

A figure F30 represents a total length of a period in which light is incident to pixels 54 by turning-on the light source of the illumination unit 29 in each pixel 54 of the imaging area 28*a*. A vertical position of the figure F30 represents the row position of the pixel 54. A horizontal width of the figure F30 is a total length of a period in which light is incident to the pixels 54 by turning-on the light source of the illumination unit 29. The total time in the incomplete exposure area 281*a* and the incomplete exposure area 281*b* are substantially the same as the total time in the complete exposure area 280*a*, the complete exposure area 280*b*, and the complete exposure area 280*c*.

In a case in which turning-on times are the same in the turning-on of three times, the light quantities of the turning-on of the three times are the same. The illumination control unit 46 may execute control such that integrated values of the turning-on times and light quantities are the same in the turning-on of three times.

In the operation represented in the graph G30, the control unit 47 sets the entire imaging area 28*a* as the scanning area. A gain regarding imaging signals of pixels 54 of the incomplete exposure area 281*c* and the incomplete exposure area 281*d* may be set to a value larger than a gain regarding imaging signals of pixels 54 of the other areas. The control unit 47 may set an area acquired by excluding the incomplete exposure area 281*c* and the incomplete exposure area 281*d* from the imaging area 28*a* as the scanning area.

In the incomplete exposure area 281*a* and the incomplete exposure area 281*b*, the light source of the illumination unit 29 is turned on twice in the exposure period. For this reason, in the incomplete exposure area 281*a* and the incomplete exposure area 281*b*, exposure according to the turning-on of the light source of the illumination unit 29 is executed twice. Since the exposure is executed twice, there are cases in which blurring of a subject occurs in the image. In a case in which a subject and the tip end part 21 stay motionless, blurring of the subject does not occur in an image corresponding to the incomplete exposure area 281*a* and the incomplete exposure area 281*b*. For this reason, imaging signals of the pixels 54 of the incomplete exposure area 281*a* and the incomplete exposure area 281*b* can be used similar to the imaging signals of the pixels 54 of the complete exposure area. On the other hand, in a case in which a subject or the tip end part 21 is moving, blurring of the subject occurs in an image based on imaging signals of the pixels 54 of the incomplete exposure area 281*a* and the incomplete exposure area 281*b*. For this reason, there is a possibility that the accuracy of three-dimensional measurement is decreased.

The video signal generating unit 41 detects moving of a subject on the basis of imaging signals or video signals corresponding to the incomplete exposure area 281*a* and the incomplete exposure area 281*b*. For example, the video signal generating unit 41 calculates a contrast value of the imaging signals or the video signals. The video signal generating unit 41 detects moving of the subject on the basis of the calculated contrast value. The video signal generating unit 41 notifies a result of the detection of the moving of the subject to the control unit 47. In a case in which the moving of the subject is less than a predetermined amount, in other words, in a case in which blurring of the subject does not occur, the image display or the measurement process based on the video signals is executed.

On the other hand, in a case in which the moving of the subject is equal to or greater than the predetermined amount, in other words, in a case in which blurring of the subject occurs, the graphic image generating unit 43 generates a graphic image signal for displaying a warning message. The signal composing unit 49 composes the video signal generated by the video signal generating unit 41 and the graphic image signal generated by the graphic image generating unit 43. The monitor 4 displays an image including a warning message on the basis of the video signal output from the signal composing unit 49. In this way, a user can know that blurring of the subject occurs. In a case in which the warning message is displayed, the user may perform a countermeasure for suppressing a decrease in the accuracy of the three-dimensional measurement.

In a case in which the endoscope apparatus 1 has an audio output function, and blurring of the subject occurs, the endoscope apparatus 1 may output the warning using voice. In a case in which the endoscope apparatus 1 has a light source for warning display, and blurring of the subject occurs, the endoscope apparatus 1 may turn on the light source for warning display. A meaning generating a warning is not limited to the means described above.

In the operation represented in the graph G30, the light source of the illumination unit 29 is turned on three times in the frame period. In addition, the light source of the illumination unit 29 may be turned on twice in the frame period. Furthermore, the light source of the illumination unit 29 may be turned on four times or more in the frame period.

In the operation represented in the graph G30, the entire imaging area 28*a* is set as the scanning area, and the light source of the illumination unit 29 is turned on three times. The imaging area 28*a* may be divided into a plurality of scanning areas, and scanning of each of the scanning areas and turning-on of the light source of the illumination unit 29 may be sequentially executed. For example, the imaging area 28a is divided into three scanning areas. The incomplete exposure area 281c, the complete exposure area 280b, and the incomplete exposure area 281a are set as a first scanning area. In addition, the incomplete exposure area 281a, the complete exposure area 280a, and the incomplete exposure area 281b are set as a second scanning area. The incomplete exposure area 281b, the complete exposure area 280c, and the incomplete exposure area 281d are set as a third scanning area. The scanning of the first scanning area and the turning-on of the light source of the illumination unit 29 are executed. Thereafter, the scanning of the second scanning area and the turning-on of the light source of the illumination unit 29 are executed. Thereafter, the scanning of the third scanning area and the turning-on of the light source of the illumination unit 29 are executed. In this way, the endoscope apparatus 1 can execute an operation similar to the operation represented in the graph G30.

As described above, the illumination control unit 46 may control the illumination unit 29 such that the light source is intermittently turned on plural times, and such that at least parts of exposure periods of pixels 54 disposed in at least a part of the scanning area in each of periods of plural times of turning-on periods overlap each other. The illumination control unit 46 may control the illumination unit 29 such that the light quantities of illumination light in the plural times of turning-on are the same. The illumination control unit 46 may control the illumination unit 29 such that the turning-on times are the same in the plural times of turning-on. In this way, variations in the exposure amounts of the pixels 54 are reduced.

An emission time may be completely included in the exposure periods of first pixels 54 of the scanning area, and only a part of the emission time may be included in the exposure periods of second pixels 54 of the scanning area. The second pixels 54 are different from the first pixels 54. The emission time is a length of a period in which illumination light is emitted to a subject in accordance with intermittent turning-on of the light source once. In such a case, the illumination control unit 46 may control the illumination unit 29 such that a first time and a second time are the same. Here, the first time is a length of a period in which illumination light is emitted to a subject in accordance with intermittent turning-on of the light source once in the exposure periods of the first pixels 54. In addition, the second time is a sum of a plurality of lengths of periods in which illumination light is emitted to a subject in accordance with plural times of intermittent turning-on of the light source in the exposure periods of the second pixels 54. In this way, variations in the exposure amounts of the first pixels 54 and the second pixels 54 are decreased.

In the operation represented in the graph G30, the first pixels 54 are pixels 54 of the complete exposure area 280a, the complete exposure area 280b, and the complete exposure area 280c. In the operation represented in the graph G30, the second pixels 54 are pixels 54 of the incomplete exposure area 281a and the incomplete exposure area 281b.

As described above, the video signal generating unit 41 (motion detector) may detect a motion (blurring) of a subject on the basis of imaging signals read from the second pixels 54 or video signals generated from the imaging signals read from the second pixels 54. The monitor 4 (warning generator) may generate a warning in a case in which the motion of the subject has a predetermined amount or more.

The operation of the endoscope apparatus 1 according to an operation mode will be described. Hereinafter, examples of the operations of the endoscope apparatus 1 in the observation mode M1 and the observation/measurement mode M2 will be described.

Figure 12:
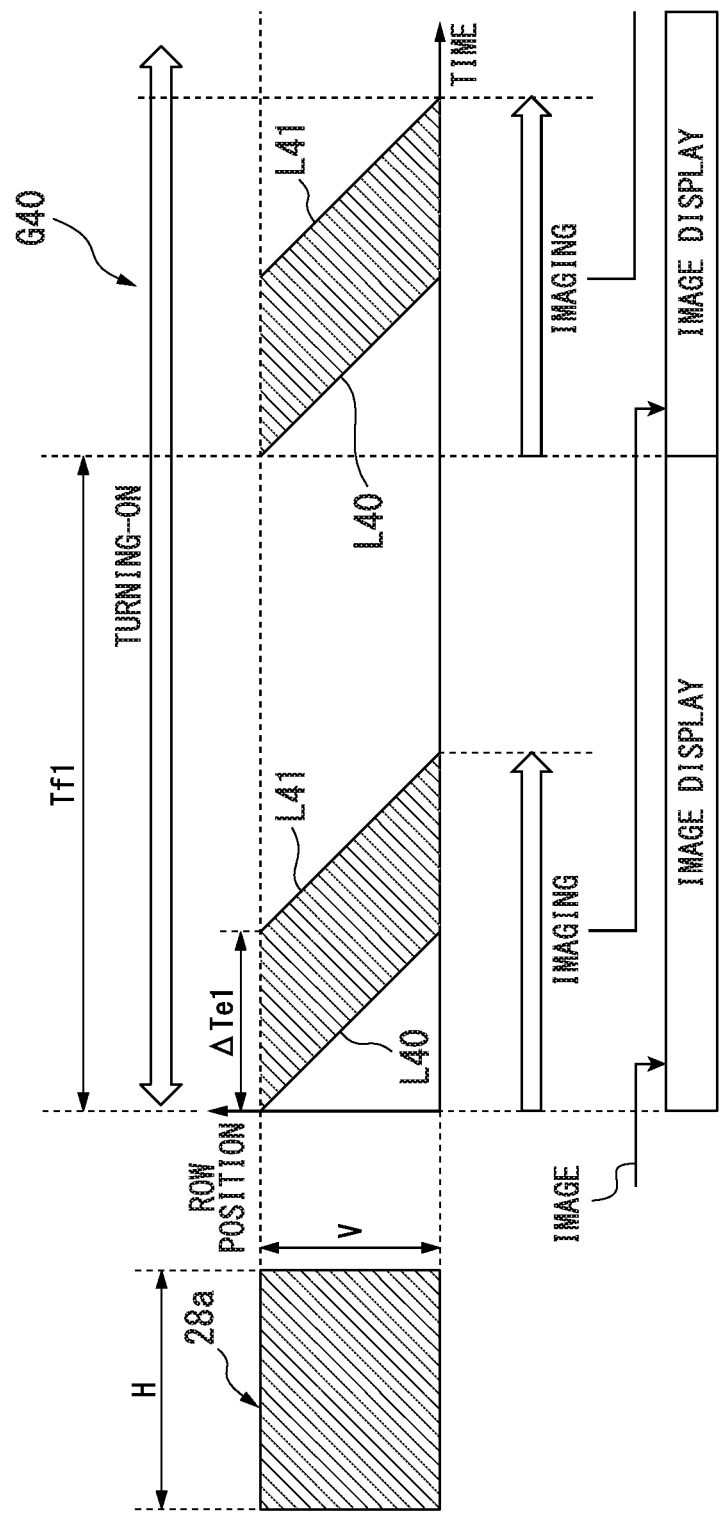
FIG. 12 is a timing chart showing the operation of an endoscope apparatus according to an embodiment of the present invention.

FIG. 12 shows a first operation of the endoscope apparatus 1 of a case in which the observation mode M1 is set. The number of horizontal pixels, in other words, the number of columns of the imaging area 28a is H. The number of vertical pixels, in other words, the number of rows of the imaging area 28a is V. In FIG. 12, a graph G40 represents the timings of the operations of pixels 54 of the imaging area 28a. In the graph G40, the horizontal direction represents the time, and the vertical direction represents the row position. The uppermost row is the first row, and the lowermost row is the V-th row.

In the observation mode M1, the control unit 47 sets the entire imaging area 28a as the scanning area. In the observation mode M1, the illumination control unit 46 controls the illumination unit 29 such that the LED 29a is continuously controlled to be turned on.

A straight line L40 represents an end timing of resetting, in other words, a start timing of exposure in the pixels 54 of each row disposed in the imaging area 28a. A straight line L41 represents a start timing of transmission of electric charge, in other words, an end timing of exposure in the pixels 54 of each row disposed in the imaging area 28a. The slope of the straight line L40 and the straight line L41 is based on the scanning rate. An exposure period is a period from a timing represented by the straight line L40 to a timing represented by the straight line L41. The length of the exposure period, in other words, an exposure time is $\Delta Te1$. The length of the frame period, in other words, the display period of the monitor 4 is Tf1. A frame rate for displaying a live image is 1/Tf1.

In the operation represented in the graph G40, the entire imaging area 28a is the scanning area. Resetting, transmission of electric charge, and signal reading are executed in the pixels 54 of all of the rows disposed in the imaging area 28a. In the operation represented in the graph G40, the same operation is repeatedly executed in a plurality of frame periods. In the operation represented in the graph G40, the image display in each frame period is executed on the basis of video signals generated from imaging signals acquired in the previous frame period.

Figure 13:
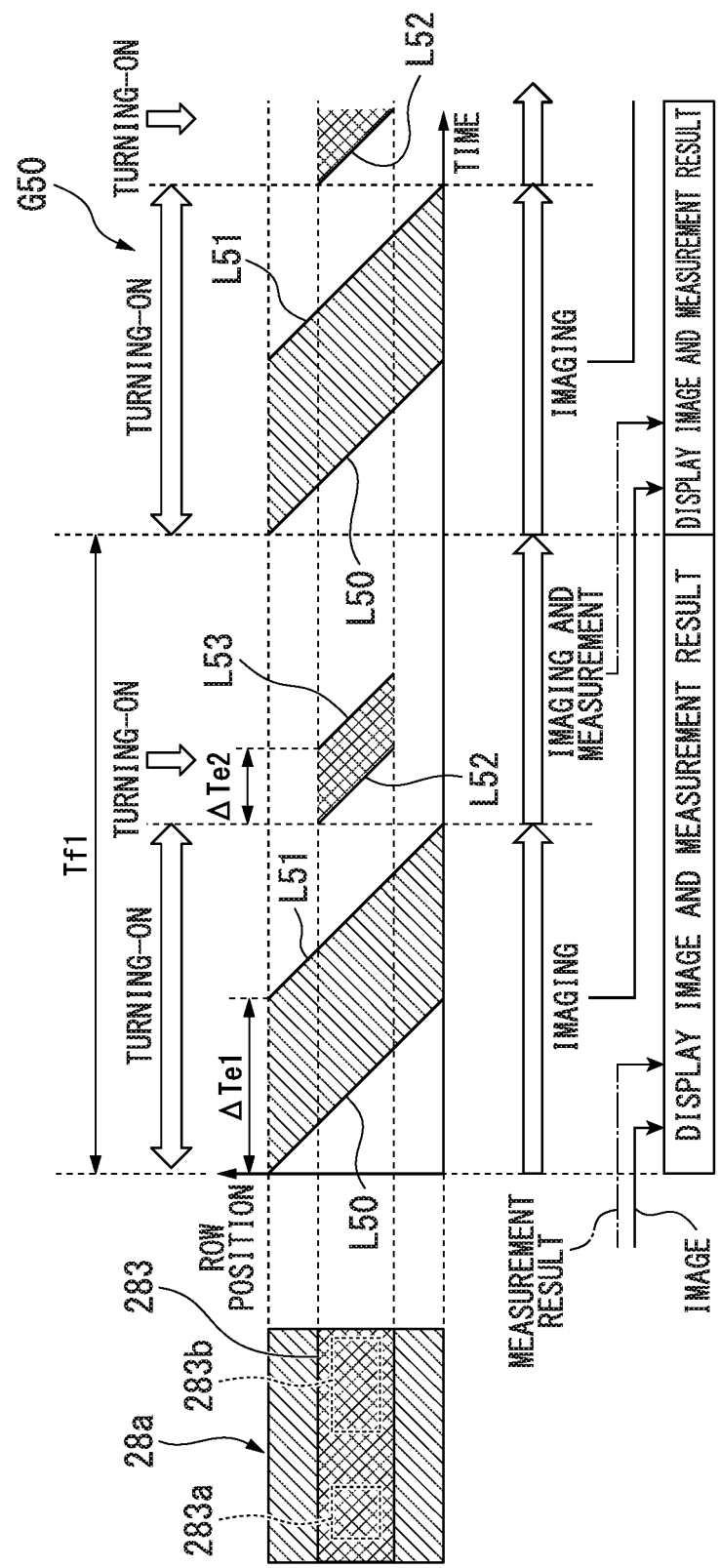
FIG. 13 is a timing chart showing the operation of an endoscope apparatus according to an embodiment of the present invention.

FIG. 13 shows a second operation of the endoscope apparatus 1 of a case in which the observation/measurement mode M2 is set. In FIG. 13, a graph G50 represents the timings of the operations of the pixels 54 of the imaging area 28a. In the graph G50, the horizontal direction represents the time, and the vertical direction represents the row position. The uppermost row is the first row, and the lowermost row is the V-th row.

In the observation/measurement mode M2, the imaging element 28 alternately executes imaging for the image display and imaging for the measurement process. The imaging element 28 executes imaging for the image display and imaging for the measurement process on one frame period. A scanning area in the imaging for the image display and a scanning area in the imaging for the measurement process are different from each other. In other words, the scanning area is changed within the frame period.

In a first period in which the imaging for the image display is executed, the control unit 47 sets the entire imaging area 28a as the scanning area. In the first period, the illumination control unit 46 controls the illumination unit 29 such that the LED 29a is continuously controlled to be turned on.

A straight line L50 represents an end timing of resetting, in other words, a start timing of exposure in the pixels 54 of each row disposed in the imaging area 28a. A straight line L51 represents a start timing of transmission of electric charge, in other words, an end timing of exposure in the pixels 54 of each row disposed in the imaging area 28a. The slope of the straight line L50 and the straight line L51 is based on the scanning rate. An exposure period is a period from a timing represented by the straight line L50 to a timing represented by the straight line L51. The length of the exposure period, in other words, an exposure time is $\Delta$Te1. The length of the frame period, in other words, the display period of the monitor 4 is Tf1. A frame rate for displaying a live image is 1/Tf1.

In the first period, the entire imaging area 28a is the scanning area. Resetting, transmission of electric charge, and signal reading are executed in the pixels 54 of all of the rows disposed in the imaging area 28a. In the first period, before resetting starts in the pixels 54 of the first row, the illumination control unit 46 turns on the LED 29a. In the first period, after transmission of electric charge in the pixels 54 of the V-th row is executed, the illumination control unit 46 turns off the LED 29a.

In a second period in which the imaging for the measurement process is executed, the control unit 47 sets a part of the imaging area 28a as the scanning area. For example, in stereo measurement, an area 283 is set as the scanning area. The area 283 includes an area 283a corresponding to the position of a measurement point and an area 283b corresponding to the position of a correspondence point. In the second period, the illumination control unit 46 controls the illumination unit 29 such that the LED 29a is intermittently turned on.

A straight line L52 represents an end timing of resetting, in other words, a start timing of exposure in the pixels 54 of each row disposed in the imaging area 283. A straight line L53 represents a start timing of transmission of electric charge, in other words, an end timing of exposure in the pixels 54 of each row disposed in the imaging area 283. The slope of the straight line L52 and the straight line L53 is based on the scanning rate. In the second period, the scanning rate is the same as the scanning rate in the first period. An exposure period is a period from a timing represented by the straight line L52 to a timing represented by the straight line L53. The length of the exposure period, in other words, an exposure time is $\Delta$Te2.

In the second period, at least parts of the exposure periods of all of the pixels 54 disposed in the area 283 overlap each other. The illumination control unit 46 intermittently turns on the LED 29a in a period in which at least parts of the exposure periods of all of the pixels 54 disposed in the area 283 overlap each other. By intermittently turning on the LED 29b, a pattern may be projected onto the subject. The number of rows of the area 283 is less than the number of rows of the imaging area 28a. For this reason, an exposure time that is necessary for at least parts of the exposure periods of all of the pixels 54 disposed in the area 283 to overlap each other may be short. The exposure time $\Delta$Te2 of the second period is shorter than the exposure time $\Delta$Te1 of the first period.

Since the exposure time $\Delta$Te2 is shorter than the exposure time $\Delta$Te1, the light quantity of the light source in the second period may be larger than the light quantity of the light source of the first period. In other words, the illumination control unit 46 may control the light quantity of the light source in the second period to be larger than the light quantity of the light source in the first period. Alternatively, a gain for imaging signals read from the pixels 54 in the second period may be larger than a gain for imaging signals read from the pixels 54 in the first period. In other words, the control unit 47 may control a second gain to be larger than a first gain. The second gain is a gain when imaging signals read from the pixels 54 in the second period are amplified by the video signal generating unit 41 or the signal processing unit 52. The first gain is a gain when imaging signals read from the pixels 54 in the first period are amplified by the video signal generating unit 41 or the signal processing unit 52.

In the second period, the area 283 is the scanning area. Resetting, transmission of electric charge, and signal reading are executed in the pixels 54 of all of the rows disposed in the area 283. In the second period, by using block reading, signal reading may be executed only in the pixels 54 of columns corresponding to the area 283a and the area 283b. In other words, resetting and transmission of electric charge may be executed in the pixels 54 of all of the rows disposed in the area 283, and signal reading may be executed only in pixels 54 of columns corresponding to the area 283a and the area 283b.

The measurement processing unit 44 executes the measurement process on the basis of the video signals generated from imaging signals output from the pixels 54 of the area 283 in the second period. The measurement processing unit 44 notifies a result of the measurement to the graphic image generating unit 43. The graphic image generating unit 43 generates a graphic image signal used for displaying the result of the measurement. The video signals generated from imaging signals output from the pixels 54 of the imaging area 28a in the first period are output to the signal composing unit 49. The signal composing unit 49 composes video signals generated by the video signal generating unit 41 and the graphic image signal generated by the graphic image generating unit 43. The monitor 4 displays an image including the result of the measurement on the basis of the video signal output from the signal composing unit 49.

In an operation represented in the graph G50, the same operation is repeatedly executed in a plurality of frame periods. In the operation represented in the graph G50, the image display in each frame period is executed on the basis of video signals generated from imaging signals acquired in the first period of the previous frame period.

The plurality of operation modes include an operation mode in which at least the image display and the measurement process are executed. In a case in which the operation mode in which at least the image display and the measurement process are executed is set, the control unit 47 controls the imaging element 28 to alternately output a first imaging signal and a second imaging signal. The first imaging signal is for one image used for the image display. The second imaging signal is for one or more images used for the measurement process. The monitor 4 displays the one image on the basis of the video signal generated from the first imaging signal. The measurement processing unit 44 executes the measurement process on the basis of the video signal generated from the second imaging signal and corresponding to the one or more images.

In the operation represented in the graph G50, the observation/measurement mode M2 is set. The control unit 47 controls the imaging element 28 to alternately output the imaging signals for one image used for the image display and the imaging signals for one image used for the measurement process. In this way, the imaging element 28 outputs the imaging signals for one image used for the image display in the first period and outputs the imaging signals for one image used for the measurement process in the second period. Accordingly, the endoscope apparatus 1 can execute the measurement process in real time.

Figure 14:
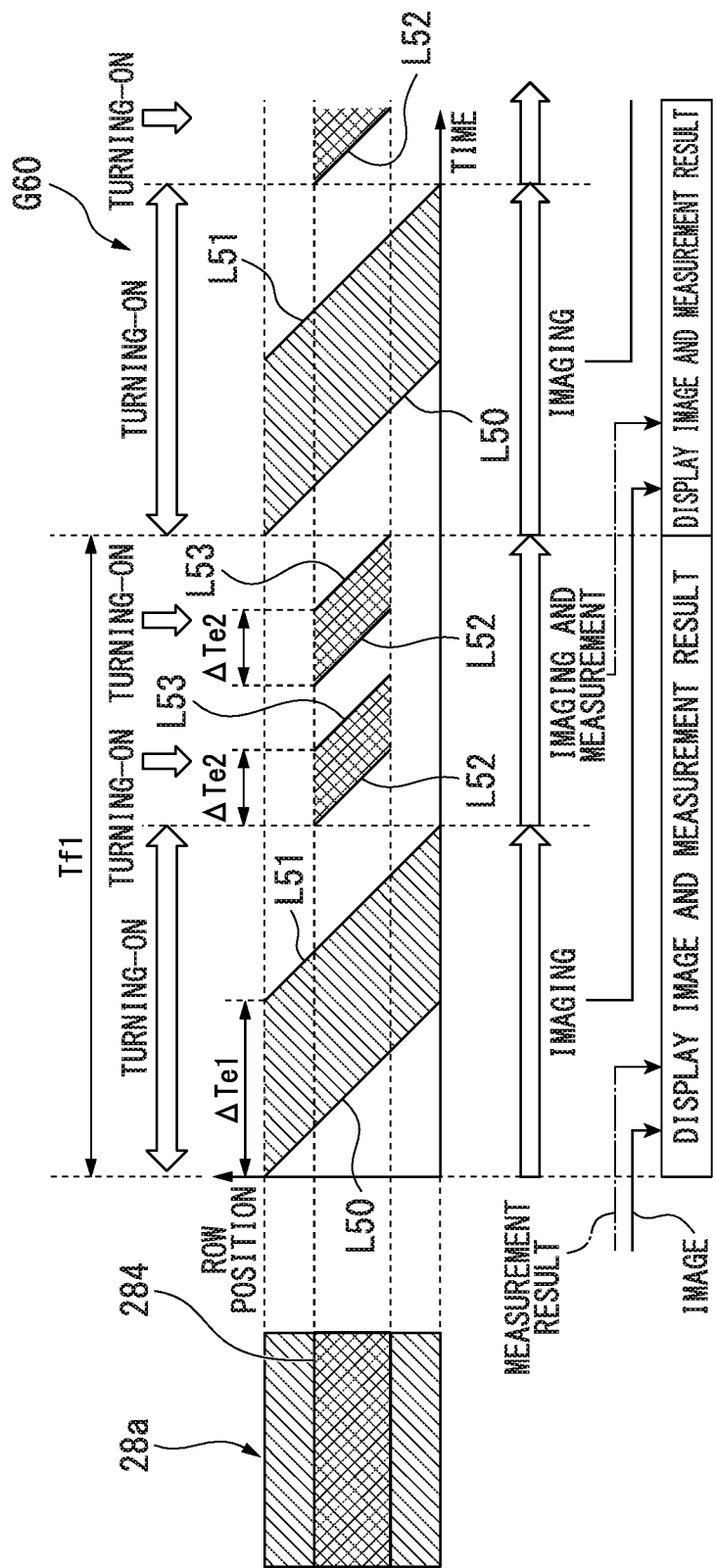
FIG. 14 is a timing chart showing the operation of an endoscope apparatus according to an embodiment of the present invention.

FIG. 14 shows a third operation of the endoscope apparatus 1 of a case in which the observation/measurement mode M2 is set. In FIG. 14, a graph G60 represents the timings of the operations of the pixels 54 of the imaging area 28a. In the graph G60, the horizontal direction represents the time, and the vertical direction represents the row position. The uppermost row is the first row, and the lowermost row is the V-th row.

In a first period in which the imaging for the image display is executed, the control unit 47 sets the entire imaging area 28a as the scanning area. In the first period, the illumination control unit 46 controls the illumination unit 29 such that the LED 29a is continuously controlled to be turned on.

The control of the imaging element 28 in the first period in the operation represented in the graph G60 is similar to the control of the imaging element 28 in the first period in the operation represented in the graph G50. The control of the illumination unit 29 in the first period in the operation represented in the graph G60 is similar to the control of the illumination unit 29 in the first period in the operation represented in the graph G50. For this reason, the control of the imaging element 28 and the illumination unit 29 in the first period will not be described.

In a second period in which imaging for the measurement process is executed, the control unit 47 sets a part of the imaging area 28a as the scanning area. In the operation represented in the graph G60, an area 284 is set as the scanning area. For example, the area 284 is the same as the area 283. In the second period, the illumination control unit 46 controls the illumination unit 29 such that the LED 29a is intermittently turned on.

In the second period, plural times of scanning of the area 284 are executed, and plural times of turning-on of the LED 29a are executed. The LED 29a is turned on at the timing at which the scanning of the area 284 is executed. In other words, in the second period, plural times of scanning that is similar to the scanning of the area 283 in the operation represented in the graph G50 in the second period are executed. In addition, in the second period, plural times of turning-on that is similar to the turning-on of the LED 29a in the second period in the operation represented in the graph G50 are executed. For this reason, the control of the imaging element 28 and illumination unit 29 in the second period will not be described here.

The measurement processing unit 44 executes the measurement process on the basis of a plurality of video signals generated from imaging signals output from the pixels 54 of the area 284 in the second period. For example, the measurement processing unit 44 averages a plurality of measurement results acquired by measurement processes based on the plurality of video signals. By averaging the plurality of measurement results, a decrease in the measurement accuracy is suppressed. In a case in which a first optical image and a second optical image having parallax are alternately formed in the imaging element 28, the scanning of the area 284 and the turning-on of the LED 29a are executed when each of the first optical image and the second optical image is formed in the imaging element 28. The measurement processing unit 44 executes the measurement process on the basis of the video signal corresponding to the first optical image and the video signal corresponding to the second optical image.

The measurement processing unit 44 notifies a measurement result to the graphic image generating unit 43. The graphic image generating unit 43 generates a graphic image signal used for displaying the measurement result. Video signals generated from the imaging signals output from the pixels 54 of the imaging area 28a in the first period are output to the signal composing unit 49. The signal composing unit 49 composes video signals generated by the video signal generating unit 41 and the graphic image signal generated by the graphic image generating unit 43. The monitor 4 displays an image including the measurement result on the basis of the video signal output from the signal composing unit 49.

In the operation represented in the graph G60, the same operation is repeatedly executed in a plurality of frame periods. In the operation represented in the graph G60, the image display in each frame period is executed on the basis of video signals generated from imaging signals acquired in the first period of the previous frame period.

In the operation represented in the graph G60, the exposure time ΔTe2 is shorter than the exposure time ΔTe1. For this reason, the illumination control unit 46 may control the light quantity of the light source in the second period to be larger than the light quantity of the light source in the first period. Alternatively, the control unit 47 may control a second gain to be larger than a first gain. Here, the second gain is a gain when imaging signals read from the pixels 54 in the second period are amplified by the video signal generating unit 41 or the signal processing unit 52. The first gain is a gain when imaging signals read from the pixels 54 in the first period are amplified by the video signal generating unit 41 or the signal processing unit 52.

In the operation represented in the graph G60, the observation/measurement mode M2 is set. The control unit 47 controls the imaging element 28 to alternately output the imaging signals for one image used for the image display and the imaging signals for two images used for the measurement process. In this way, the imaging element 28 outputs the imaging signals for one image used for the image display in the first period and outputs the imaging signals for two images used for the measurement process in the second period. Accordingly, the endoscope apparatus 1 can execute the measurement process in real time.

In the operation represented in the graph G60, imaging and intermittent turning-on of the LED 29a are executed twice in the first frame period. In addition, imaging and intermittent turning-on of the LED 29a may be executed three times or more in one frame period.

Figure 15:
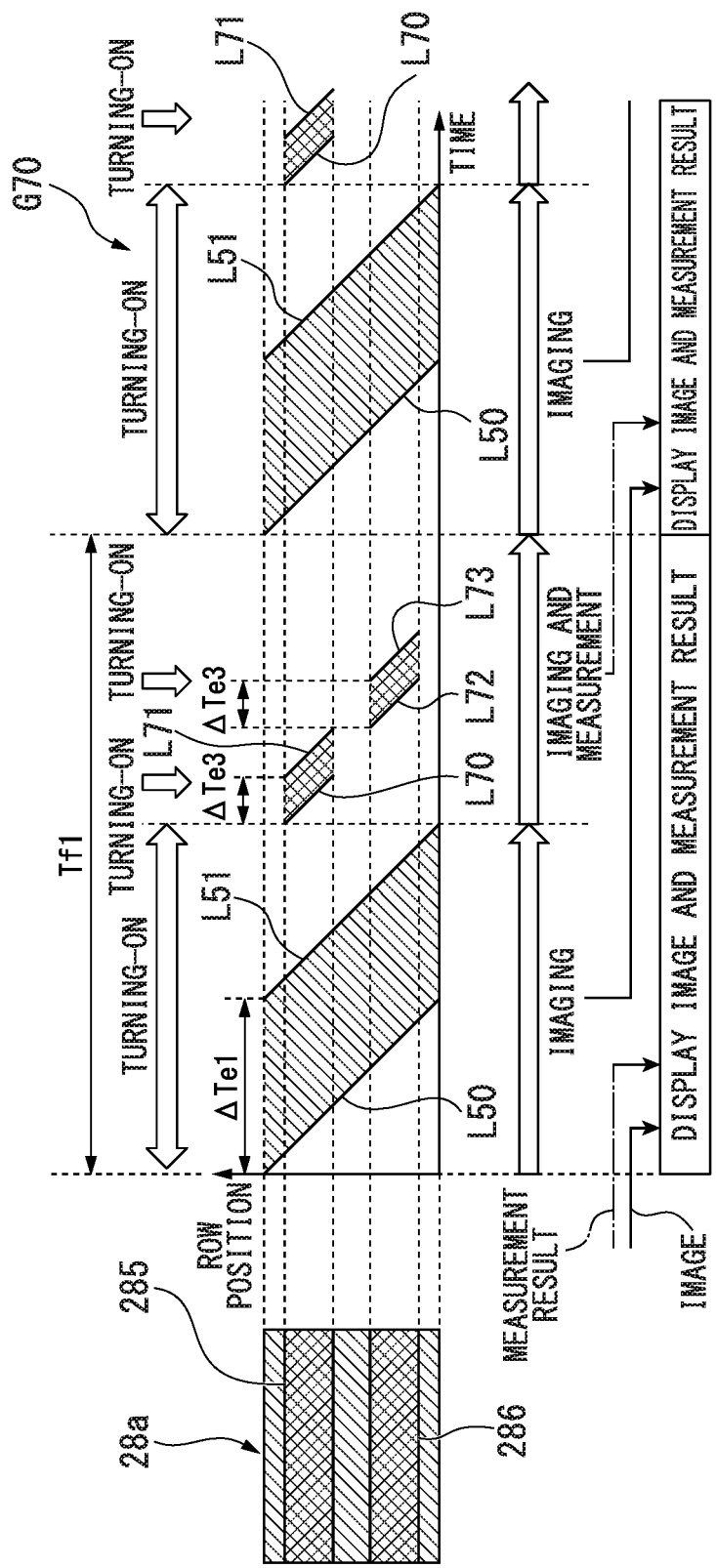
FIG. 15 is a timing chart showing the operation of an endoscope apparatus according to an embodiment of the present invention.

FIG. 15 shows a fourth operation of the endoscope apparatus 1 of a case in which the observation/measurement mode M2 is set. In FIG. 15, a graph G70 represents the timings of the operations of the pixels 54 of the imaging area 28a. In the graph G70, the horizontal direction represents the time, and the vertical direction represents the row position. The uppermost row is the first row, and the lowermost row is the V-th row.

In a first period in which the imaging for the image display is executed, the control unit 47 sets the entire imaging area 28a as the scanning area. In the first period, the illumination control unit 46 controls the illumination unit 29 such that the LED 29a is continuously controlled to be turned on.

The control of the imaging element 28 in the first period in the operation represented in the graph G70 is similar to the control of the imaging element 28 in the first period in the operation represented in the graph G50. The control of the illumination unit 29 in the first period in the operation represented in the graph G70 is similar to the control of the illumination unit 29 in the first period in the operation represented in the graph G50. For this reason, the control of the imaging element 28 and the illumination unit 29 in the first period will not be described.

In a second period in which imaging for the measurement process is executed, the control unit 47 sets a part of the imaging area 28a as the scanning area. In the operation represented in the graph G70, the imaging area 28a includes a plurality of scanning areas. In the operation represented in the graph G70, an area 285 and an area 286 are set as the scanning area. The area 285 is disposed on the upper side, and the area 286 is disposed on the lower side. The area 285 and the area 286 do not overlap each other. In the second period, the illumination control unit 46 controls the illumination unit 29 such that the LED 29a is intermittently turned on.

The endoscope apparatus 1 includes the measurement processing unit 44 that executes the measurement process on the basis of video signals. The plurality of operation modes includes an operation mode in which at least the measurement process is executed. In the operation represented in the graph G70, in a case in which an operation mode in which at least the measurement process is executed is set and a plurality of measurement points are set, the control unit 47 sets a plurality of scanning areas to include the pixel 54 at which each of the plurality of measurement points is set. For example, in the operation represented in the graph G70, two measurement points are designated. The area 285 and the area 286 are set such that the pixels 54 at which the two measurement points are set are included in mutually-different areas. In this way, the endoscope apparatus 1 can acquire an image of an area that is necessary for the measurement process in a case in which a plurality of measurement points are set.

A straight line L70 represents an end timing of resetting, in other words, a start timing of exposure in the pixels 54 of each row disposed in the area 285. A straight line L71 represents a start timing of transmission of electric charge, in other words, an end timing of exposure in the pixels 54 of each row disposed in the area 285. A straight line L72 represents an end timing of resetting, in other words, a start timing of exposure in the pixels 54 of each row disposed in the area 286. A straight line L73 represents a start timing of transmission of electric charge, in other words, an end timing of exposure in the pixels 54 of each row disposed in the area 286. The slope of the straight line L70, the straight line L71, the straight line L72, and the straight line L73 is based on the scanning rate. The scanning rate in the second period is the same as the scanning rate in the first period. An exposure period is a period from a timing represented by the straight line L70 and the straight line L72 to a timing represented by the straight line L71 and the straight line L73. The length of the exposure period, in other words, an exposure time is $\Delta Te3$.

In the second period, at least parts of the exposure periods of all of the pixels 54 disposed in the area 285 overlap each other. In addition, in the second period, at least parts of the exposure periods of all of the pixels 54 disposed in the area 286 overlap each other. The illumination control unit 46 intermittently turns on the LED 29a in a period in which at least parts of the exposure periods of all of the pixels 54 disposed in the area 285 overlap each other. Thereafter, the illumination control unit 46 intermittently turns on the LED 29a in a period in which at least parts of the exposure periods of all of the pixels 54 disposed in the area 286 overlap each other. By intermittently turning on the LED 29b, a pattern may be projected onto the subject. The number of rows of each of the area 285 and the area 286 is less than the number of rows of the imaging area 28a. For this reason, an exposure time that is necessary for at least parts of the exposure periods of all of the pixels 54 disposed in each of the area 285 and the area 286 to overlap each other may be short. The exposure time $\Delta Te3$ of the second period is shorter than the exposure time $\Delta Te1$ of the first period.

In the second period, the area 285 and the area 286 are the scanning area. Resetting, transmission of electric charge, and signal reading are executed in the pixels 54 of all of the rows disposed in the area 285 and 286. In the second period, by using block reading, signal reading may be executed only in the pixels 54 of a part of columns disposed in the area 285 and the area 286. In other words, resetting and transmission of electric charge may be executed in the pixels 54 of all of the rows disposed in the area 285 and the area 286, and signal reading may be executed only in pixels 54 of a part of columns disposed in the area 285 and the area 286.

The measurement processing unit 44 executes the measurement process on the basis of the video signals generated from the imaging signals output from the pixels 54 of the area 285 and the area 286 in the second period. The measurement processing unit 44 notifies a result of the measurement to the graphic image generating unit 43. The graphic image generating unit 43 generates a graphic image signal used for displaying the result of the measurement. The video signals generated from imaging signals output from the pixels 54 of the imaging area 28a in the first period are output to the signal composing unit 49. The signal composing unit 49 composes video signals generated by the video signal generating unit 41 and the graphic image signal generated by the graphic image generating unit 43. The monitor 4 displays an image including the result of the measurement on the basis of the video signal output from the signal composing unit 49.

In an operation represented in the graph G70, the same operation is repeatedly executed in a plurality of frame periods. In the operation represented in the graph G70, the image display in each frame period is executed on the basis of video signals generated from imaging signals acquired in the first period of the previous frame period.

In the operation represented in the graph G70, the exposure time $\Delta Te3$ is shorter than the exposure time $\Delta Te1$. For this reason, the illumination control unit 46 may control the light quantity of the light source in the second period to be larger than the light quantity of the light source in the first period. Alternatively, the control unit 47 may control a second gain to be larger than a first gain. Here, the second gain is a gain when imaging signals read from the pixels 54 in the second period are amplified by the video signal generating unit 41 or the signal processing unit 52. The first gain is a gain when imaging signals read from the pixels 54 in the first period are amplified by the video signal generating unit 41 or the signal processing unit 52.

In the operation represented in the graph G70, the observation/measurement mode M2 is set. The control unit 47 controls the imaging element 28 to alternately output the imaging signals for one image used for the image display and the imaging signals for two images used for the measurement process. In this way, the imaging element 28 outputs the imaging signals for one image used for the image display in the first period and outputs the imaging signals for two images used for the measurement process in the second period. Accordingly, the endoscope apparatus 1 can execute the measurement process in real time.

In the operation represented in the graph G70, the imaging area 28a in the second period includes two scanning areas. The imaging area 28a in the second period may include three scanning areas or more.

In the operation represented in the Graph G70, imaging in each of the area 285 and the area 286 and intermittent turning-on of the LED 29a are executed once in the second period. In the second period, imaging in each of the area 285 and the area 286 and intermittent turning-on of the LED 29a may be executed two times or more.

Figure 16:
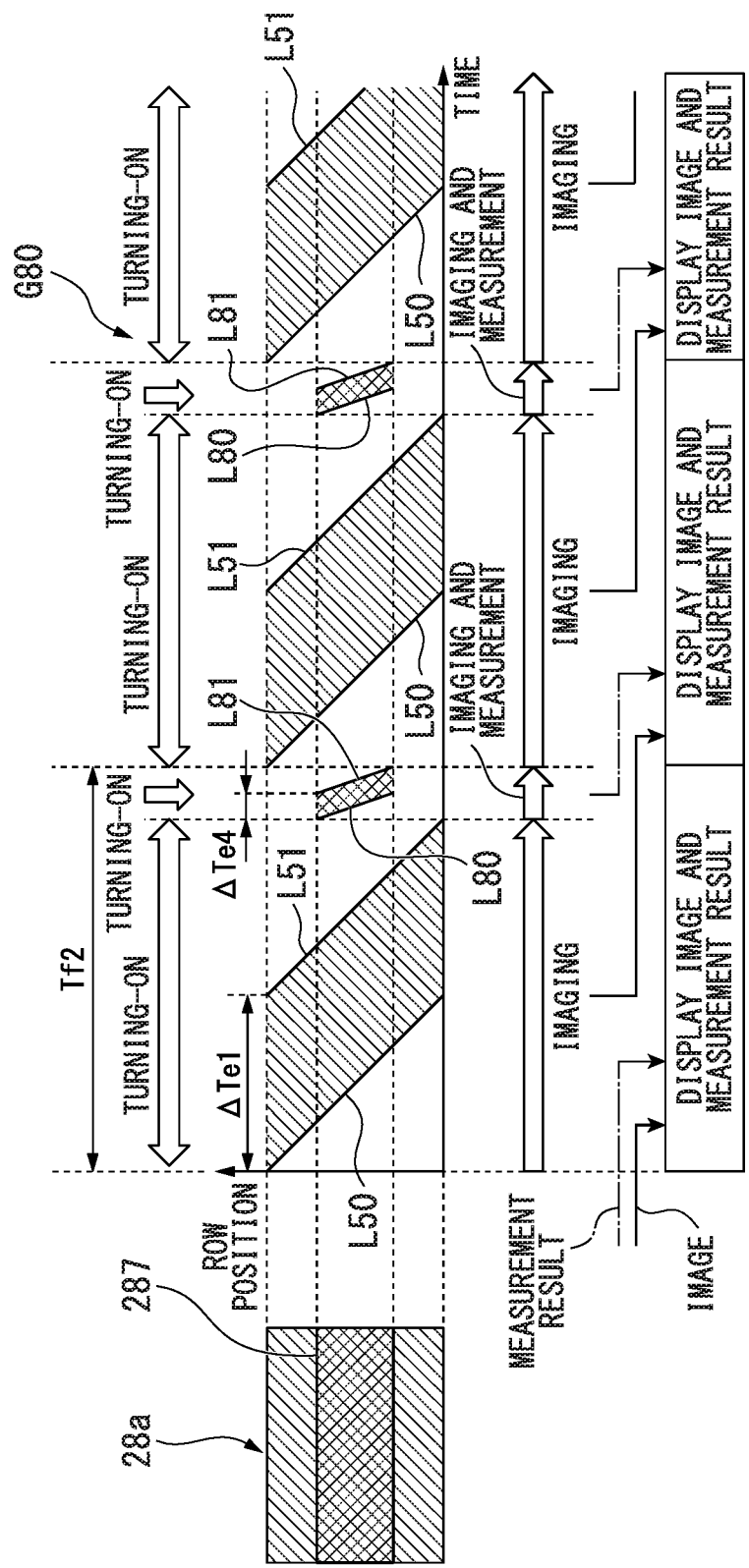
FIG. 16 is a timing chart showing the operation of an endoscope apparatus according to an embodiment of the present invention.

FIG. 16 shows a fifth operation of the endoscope apparatus 1 of a case in which the observation/measurement mode M2 is set. In FIG. 16, a graph G80 represents the timings of the operations of the pixels 54 of the imaging area 28a. In the graph G80, the horizontal direction represents the time, and the vertical direction represents the row position. The uppermost row is the first row, and the lowermost row is the V-th row.

In a first period in which the imaging for the image display is executed, the control unit 47 sets the entire imaging area 28a as the scanning area. In the first period, the illumination control unit 46 controls the illumination unit 29 such that the LED 29a is continuously controlled to be turned on.

The control of the imaging element 28 in the first period in the operation represented in the graph G80 is similar to the control of the imaging element 28 in the first period in the operation represented in the graph G50. The control of the illumination unit 29 in the first period in the operation represented in the graph G80 is similar to the control of the illumination unit 29 in the first period in the operation represented in the graph G50. For this reason, the control of the imaging element 28 and the illumination unit 29 in the first period will not be described.

In a second period in which imaging for the measurement process is executed, the control unit 47 sets a part of the imaging area 28a as the scanning area. In the operation represented in the graph G80, the imaging area 287 is set as the scanning area. For example, the area 287 is the same as the area 283. In the second period, the illumination control unit 46 controls the illumination unit 29 such that the LED 29a is intermittently turned on.

A straight line L80 represents an end timing of resetting, in other words, a start timing of exposure in the pixels 54 of each row disposed in the area 287. A straight line L81 represents a start timing of transmission of electric charge, in other words, an end timing of exposure in the pixels 54 of each row disposed in the area 287. The slope of the straight line L80 and the straight line L81 is based on the scanning rate. The scanning rate in the second period is higher than the scanning rate in the first period. An exposure period is a period from a timing represented by the straight line L80 to a timing represented by the straight line L81. The length of the exposure period, in other words, an exposure time is $\Delta Te4$.

In the second period, at least parts of the exposure periods of all of the pixels 54 disposed in the area 287 overlap each other. The illumination control unit 46 intermittently turns on the LED 29a in a period in which at least parts of the exposure periods of all of the pixels 54 disposed in the area 287 overlap each other. By intermittently turning on the LED 29b, a pattern may be projected onto the subject. The number of rows of the area 287 is less than the number of rows of the imaging area 28a. For this reason, an exposure time that is necessary for at least parts of the exposure periods of all of the pixels 54 disposed in the area 287 to overlap each other may be short. The exposure time $\Delta Te4$ of the second period is shorter than the exposure time $\Delta Te1$ of the first period.

Since the scanning rate in the second period is higher than the scanning rate in the first period, the second period can be further shortened. As a result, the frame period can be shortened. In other words, the frame rate can be increased. In the operation represented in the graph G80, the length of the frame period, in other words, the display period of the monitor 4 is Tf2. Tf2 is shorter than Tf1. A frame rate for displaying a live image is 1/Tf2.

In the second period, the area 287 is the scanning area. Resetting, transmission of electric charge, and signal reading are executed in the pixels 54 of all of the rows disposed in the area 287. In the second period, by using block reading, signal reading may be executed only in the pixels 54 of only a part of columns disposed in the area 287. In other words, resetting and transmission of electric charge may be executed in the pixels 54 of all of the rows disposed in the area 287, and signal reading may be executed only in pixels 54 of a part of columns disposed in the area 287.

The measurement processing unit 44 executes the measurement process on the basis of the video signals generated from the imaging signals output from the pixels 54 of the area 287 in the second period. The measurement processing unit 44 notifies a result of the measurement to the graphic image generating unit 43. The graphic image generating unit 43 generates a graphic image signal used for displaying the result of the measurement. The video signals generated from imaging signals output from the pixels 54 of the imaging area 28a in the first period are output to the signal composing unit 49. The signal composing unit 49 composes video signals generated by the video signal generating unit 41 and the graphic image signal generated by the graphic image generating unit 43. The monitor 4 displays an image including the result of the measurement on the basis of the video signal output from the signal composing unit 49.

In an operation represented in the graph G80, the same operation is repeatedly executed in a plurality of frame periods. In the operation represented in the graph G80, the image display in each frame period is executed on the basis of video signals generated from imaging signals acquired in the first period of the previous frame period.

In the operation represented in the graph G80, the exposure time $\Delta Te4$ is shorter than the exposure time $\Delta Te1$. For this reason, the illumination control unit 46 may control the light quantity of the light source in the second period to be larger than the light quantity of the light source in the first period. Alternatively, the control unit 47 may control a second gain to be larger than a first gain. Here, the second gain is a gain when imaging signals read from the pixels 54 in the second period are amplified by the video signal generating unit 41 or the signal processing unit 52. The first gain is a gain when imaging signals read from the pixels 54 in the first period are amplified by the video signal generating unit 41 or the signal processing unit 52.

As described above, in a case in which an operation mode in which at least the measurement process is executed is set, the control unit 47 may control a first scanning rate to be larger than a second scanning rate. Here, the first scanning rate is a scanning rate for acquiring imaging signals used for a measurement process. In addition, the second scanning rate is a scanning rate for acquiring imaging signals used only for a process other than the measurement process.

In the operation represented in the graph G80, the observation/measurement mode M2 is set. The imaging signals acquired in the first period are used for the image display.

The imaging signals acquired in the second period are used for the measurement process. The control unit 47 controls the scanning rate in the second period to be larger than the scanning rate in the first period. In this way, the endoscope apparatus 1 can acquire an image at a higher frame rate. Alternatively, the endoscope apparatus 1 can acquire more images in the frame period.

In the operation represented in the graph G80, the observation/measurement mode M2 is set. The control unit 47 controls the imaging element 28 to alternately output imaging signals for one image used for the image display and imaging signals for one image used for the measurement process. In this way, the imaging element 28 outputs the imaging signals for one image used for the image display in the first period and outputs the imaging signals for one image used for the measurement process in the second period. Accordingly, the endoscope apparatus 1 can execute the measurement process in real time.

In the operation represented in the graph G80, imaging and intermittent turning-on of the LED 29a are executed once in the second period. Imaging and intermittent turning-on of the LED 29a may be executed two times or more in the second period.

Figure 17:
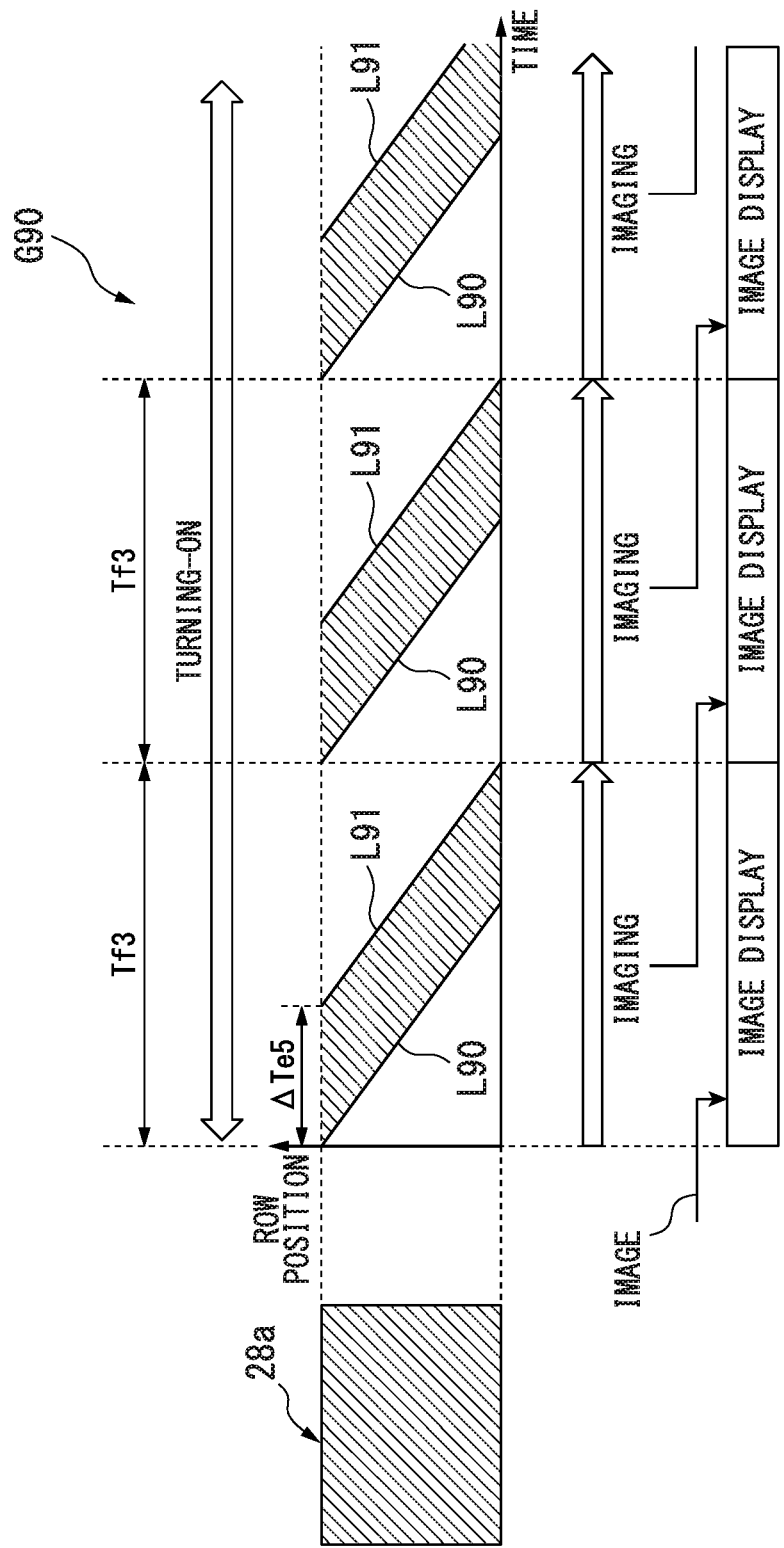
FIG. 17 is a timing chart showing the operation of an endoscope apparatus according to an embodiment of the present invention.

FIG. 17 shows a sixth operation of the endoscope apparatus 1 of a case in which the observation mode M1 is set. In FIG. 17, a graph G90 represents the timings of the operations of the pixels 54 of the imaging area 28a. In the graph G90, the horizontal direction represents the time, and the vertical direction represents the row position. The uppermost row is the first row, and the lowermost row is the V-th row.

In the observation mode M1, the control unit 47 sets the entire imaging area 28a as the scanning area. In the observation mode M1, the illumination control unit 46 controls the illumination unit 29 such that the LED 29a is continuously controlled to be turned on.

A straight line L90 represents an end timing of resetting, in other words, a start timing of exposure in the pixels 54 of each row disposed in the imaging area 28a. A straight line L91 represents a start timing of transmission of electric charge, in other words, an end tinting of exposure in the pixels 54 of each row disposed in the imaging area 28a. The slope of the straight line L90 and the straight line L91 is based on the scanning rate. An exposure period is a period from a timing represented by the straight line L90 to a timing represented by the straight line L91. The length of the exposure period, in other words, an exposure time is $\Delta Te5$. The length of the frame period, in other words, the display period of the monitor 4 is Tf3. Tf3 is shorter than Tf1. A frame rate for displaying a live image is 1/Tf3.

In the operation represented in the graph G90, the entire imaging area 28a is the scanning area. Resetting, transmission of electric charge, and signal reading are executed in the pixels 54 of all of the rows disposed in the imaging area 28a. In the operation represented in the graph G90, the same operation is repeatedly executed in a plurality of frame periods. In the operation represented in the graph G90, the image display in each frame period is executed on the basis of video signals generated from imaging signals acquired in the previous frame period.

Figure 18:
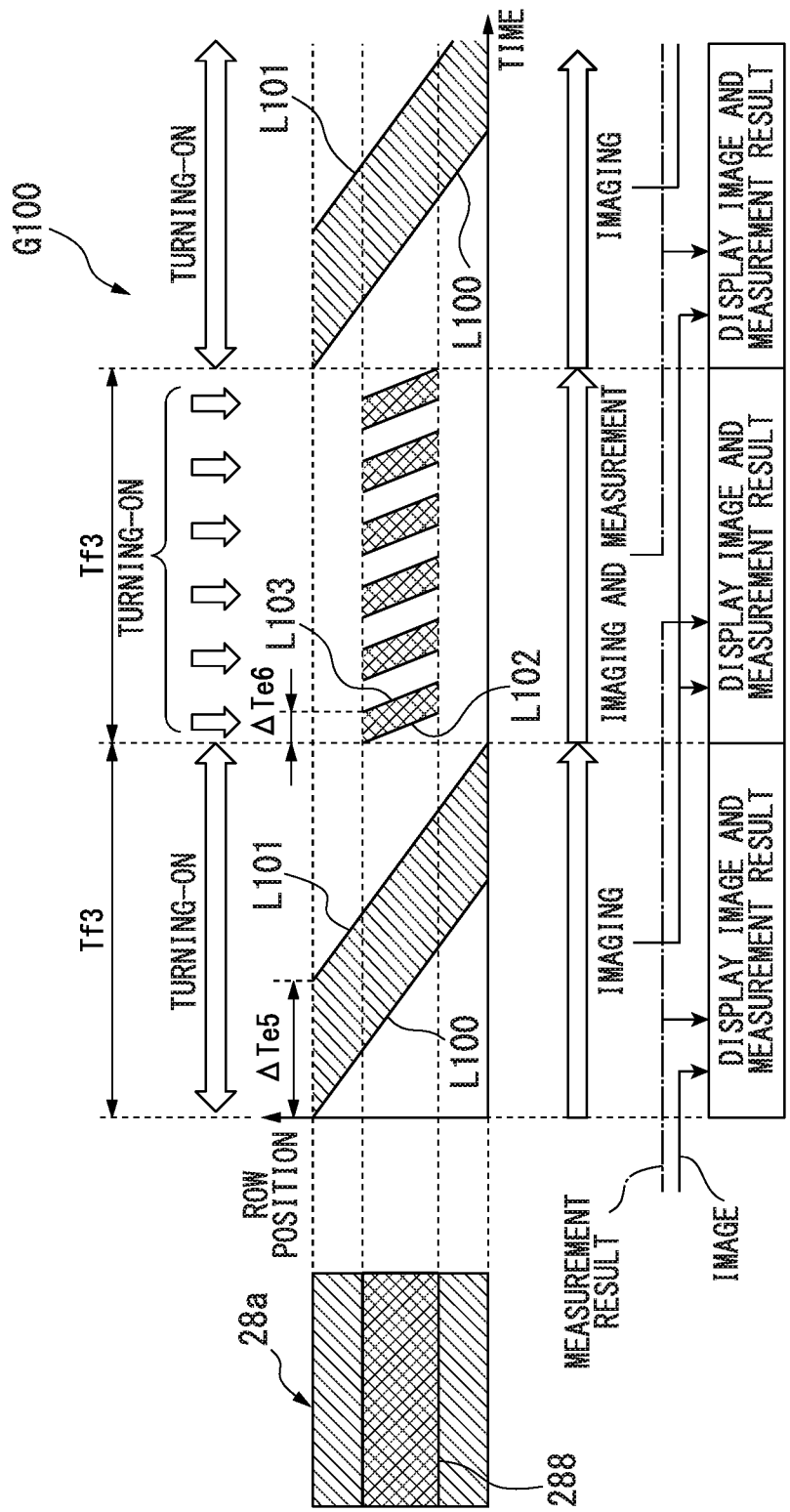
FIG. 18 is a timing chart showing the operation of an endoscope apparatus according to an embodiment of the present invention.

FIG. 18 shows a seventh operation of the endoscope apparatus 1 of a case in which the observation/measurement mode M2 is set. In FIG. 18, a graph G100 represents the timings of the operations of the pixels 54 of the imaging area 28a. In the graph G100, the horizontal direction represents the time, and the vertical direction represents the row position. The uppermost row is the first row, and the lowermost row is the V-th row.

In the observation/measurement mode M2, the imaging element 28 alternately executes imaging for the image display and imaging for the measurement process. The imaging element 28 executes imaging for image display and imaging for the measurement process in different frame periods. A scanning area in the imaging for the image display and a scanning area in the imaging for the measurement process are different from each other. In other words, the scanning area is changed for each frame.

In a first frame period in which the imaging for the image display is executed, the control unit 47 sets the entire imaging area 28a as the scanning area. In the first frame period, the illumination control unit 46 controls the illumination unit 29 such that the LED 29a is continuously controlled to be turned on.

A straight line L00 represents an end timing of resetting, in other words, a start timing of exposure in the pixels 54 of each row disposed in the imaging area 28a. A straight line L101 represents a start timing of transmission of electric charge, in other words, an end timing of exposure in the pixels 54 of each row disposed in the imaging area 28a. The slope of the straight line L100 and the straight line L101 is based on the scanning rate. An exposure period is a period from a timing represented by the straight line L100 to a tinting represented by the straight line L101. The length of the exposure period, in other words, an exposure time is $\Delta Te5$. The length of the frame period, in other words, the display period of the monitor 4 is Tf3. A frame rate for displaying a live image is 1/Tf3.

In the first frame period, the entire imaging area 28a is the scanning area. Resetting, transmission of electric charge, and signal reading are executed in the pixels 54 of all of the rows disposed in the imaging area 28a. In the first frame period, before resetting starts in the pixels 54 of the first row, the illumination control unit 46 turns on the LED 29a. In the first frame period, after transmission of electric charge in the pixels 54 of the V-th row is executed, the illumination control unit 46 turns off the LED 29a.

In a second frame period in which the imaging for the measurement process is executed, the control unit 47 sets a part of the imaging area 28a as the scanning area. For example, an area 288 is set as the scanning area. In the second period, the illumination control unit 46 controls the illumination unit 29 such that the LED 29a is intermittently turned on.

A straight line L102 represents an end timing of resetting, in other words, a start timing of exposure in the pixels 54 of each row disposed in the imaging area 288. A straight line L103 represents a start timing of transmission of electric charge, in other words, an end timing of exposure in the pixels 54 of each row disposed in the imaging area 288. The slope of the straight line L102 and the straight line L103 is based on the scanning rate. In the second frame period, the scanning rate is higher than the scanning rate in the first frame period. An exposure period is a period from a timing represented by the straight line L102 to a timing represented by the straight line L103. The length of the exposure period, in other words, an exposure time is $\Delta Te6$.

In the second frame period, at least parts of the exposure periods of all of the pixels 54 disposed in the area 288 overlap each other. The illumination control unit 46 intermittently turns on the LED 29a in a period in which at least parts of the exposure periods of all of the pixels 54 disposed in the area 288 overlap each other. By intermittently turning on the LED 29*b*, a pattern or stripes may be projected onto the subject.

In the second frame period, the scanning of the area 288 is executed plural times, and turning-on of the LED 29*a* is executed plural times. The LED 29*a* is turned on at a timing at which the area 288 is scanned.

The number of rows of the area 288 is less than the number of rows of the imaging area 28*a*. For this reason, an exposure time that is necessary for at least parts of the exposure periods of all of the pixels 54 disposed in the area 288 to overlap each other may be short. The exposure time ΔTe6 of the second frame period is shorter than the exposure time ΔTe5 of the first frame period.

In the second frame period, the area 288 is the scanning area. Resetting, transmission of electric charge, and signal reading are executed in the pixels 54 of all of the rows disposed in the area 288. In the second frame period, by using block reading, signal reading may be executed only in the pixels 54 of a part of columns disposed in the area 288. In other words, resetting and transmission of electric charge may be executed in the pixels 54 of all of the rows disposed in the area 288, and signal reading may be executed only in pixels 54 of a part of columns disposed in the area 288.

The measurement processing unit 44 executes the measurement process on the basis of a plurality of video signals generated from the imaging signals output from the pixels 54 of the area 288 in the second frame period. For example, the measurement processing unit 44 averages a plurality of measurement results acquired by measurement processes based on the plurality of video signals. By averaging the plurality of measurement results, a decrease in the measurement accuracy is suppressed. In a case in which a first optical image and a second optical image having parallax are alternately formed in the imaging element 28, the scanning of the area 288 and the turning-on of the LED 29*a* are executed when each of the first optical image and the second optical image is formed in the imaging element 28. The measurement processing unit 44 executes the measurement process on the basis of the video signal corresponding to the first optical image and the video signal corresponding to the second optical image.

The measurement processing unit 44 notifies a measurement result to the graphic image generating unit 43. The graphic image generating unit 43 generates a graphic image signal used for displaying the measurement result. Video signals generated from the imaging signals output from the pixels 54 of the imaging area 28*a* in the first frame period are output to the signal composing unit 49. The signal composing unit 49 composes video signals generated by the video signal generating unit 41 and the graphic image signal generated by the graphic image generating unit 43. The monitor 4 displays an image including the measurement result on the basis of the video signal output from the signal composing unit 49.

In the operation represented in the graph G100, operations of two continuous frame periods are repeatedly executed in a plurality of frame periods. In the operation represented in the graph G100, the image display in each frame period is executed on the basis of video signals generated from imaging signals acquired in the first frame period. The video signals generated from the imaging signals acquired in the first frame period are used for the image display in two continuous frame periods. In other words, the same image is displayed in two continuous frame periods. In the operation represented in the graph G100, a measurement result displayed in each frame period is based on the measurement process executed in the second frame period. A measurement result acquired in the second frame period is displayed in two continuous frame periods. In other words, the same measurement result is displayed in two continuous frame periods.

In the operation represented in the graph G100, the exposure time ΔTe6 is shorter than the exposure time ΔTe5. For this reason, the illumination control unit 46 may control the light quantity of the light source in the second frame period to be larger than the light quantity of the light source in the first frame period. Alternatively, the control unit 47 may control a second gain to be larger than a first gain. Here, the second gain is a gain when imaging signals read from the pixels 54 in the second frame period are amplified by the video signal generating unit 41 or the signal processing unit 52. The first gain is a gain when imaging signals read from the pixels 54 in the first frame period are amplified by the video signal generating unit 41 or the signal processing unit 52.

In the operation represented in the graph G100, the observation/measurement mode M2 is set. The imaging signals acquired in the first frame period are used for the image display. The imaging signals acquired in the second frame period are used for the measurement process. The control unit 47 controls the scanning rate in the second frame period to be larger than the scanning rate in the first frame period. In this way, the endoscope apparatus 1 can acquire more images in the second frame period.

In the operation represented in the graph G100, the observation/measurement mode M2 is set. The control unit 47 controls the imaging element 28 to alternately output imaging signals for one image used for the image display and imaging signals for six images used for the measurement process. In this way, the imaging element 28 outputs the imaging signals for one image used for the image display in the first frame period and outputs the imaging signals for six images used for the measurement process in the second frame period. Accordingly, the endoscope apparatus 1 can execute the measurement process in real time.

The control unit 47 controls the imaging element 28 to output a first imaging signal in a first display period and outputs a second imaging signal in a second display period following the first display period. The first display period and the second display period are based on the display period of the monitor 4. The monitor 4 displays the one image on the basis of video signals generated from the first imaging signals in the first display period and the second display period.

In the operation represented in the graph G100, the imaging element 28 outputs the imaging signals in the first frame period that is the first display period and the second frame period that is the second display period. The monitor 4 displays the one image on the basis of the video signal generated from imaging signals read in the first frame period in the first frame period and the second frame period. In this way, the endoscope apparatus 1 can continue to execute the image display.

In the operation represented in the graph G100, imaging and intermittent turning-on of the LED 29*a* are executed six times in the second frame period. In the second frame period, imaging and intermittent turning-on of the LED 29*a* may be executed two times to five times. In the second frame period, imaging and intermittent turning-on of the LED 29*a* may be executed seven times or more.

Figure 19:
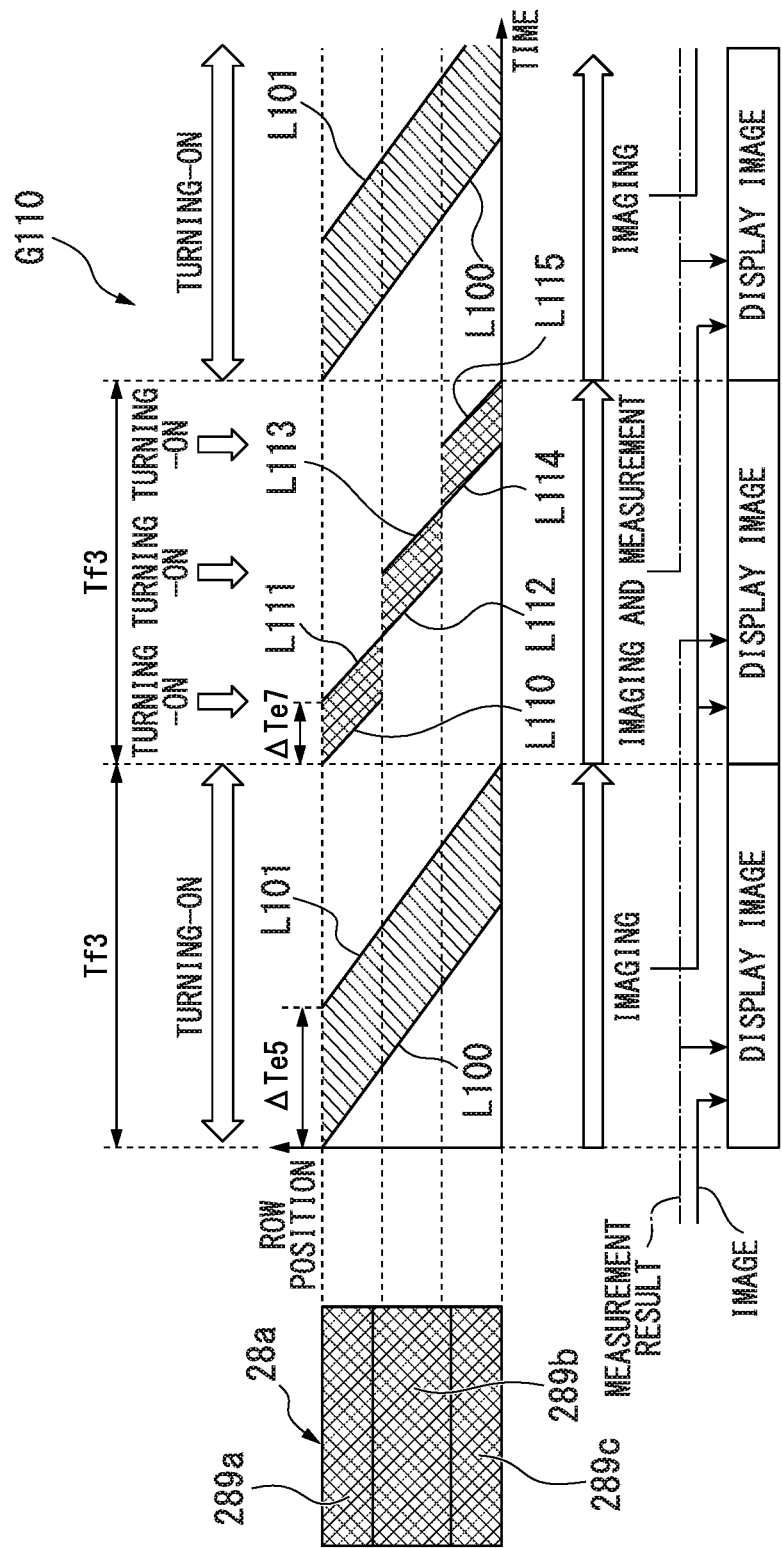
FIG. 19 is a timing chart showing the operation of an endoscope apparatus according to an embodiment of the present invention.

FIG. 19 shows an eighth operation of the endoscope apparatus 1 of a case in which the observation/measurement mode M2 is set. In FIG. 19, a graph G110 represents the timings of the operations of the pixels 54 of the imaging area 28*a*. In the graph G110, the horizontal direction represents the time, and the vertical direction represents the row position. The uppermost row is the first row, and the lowermost row is the V-th row.

In the observation/measurement mode M2, the imaging element 28 alternately executes imaging for the image display and imaging for the measurement process. The imaging element 28 executes imaging for the image display and imaging for the measurement process in different frame periods. A scanning area in the imaging for the image display and a scanning area in the imaging for the measurement process are different from each other. In other words, the scanning area is changed for each frame.

In a first frame period in which the imaging for the image display is executed, the control unit 47 sets the entire imaging area 28*a* as the scanning area. In the first frame period, the illumination control unit 46 controls the illumination unit 29 such that the LED 29*a* is continuously controlled to be turned on.

The control of the imaging element 28 in the first frame period in the operation represented in the graph G110 is similar to the control of the imaging element 28 in the first frame period in the operation represented in the graph G100. The control of the illumination unit 29 in the first frame period in the operation represented in the graph G110 is similar to the control of the illumination unit 29 in the first frame period in the operation represented in the graph G100. For this reason, the control of the imaging element 28 and the illumination unit 29 in the first frame period will not be described.

In the second frame period in which the measurement process is executed, the control unit 47 divides the imaging area 28*a* into a plurality of scanning areas. In the operation represented in the graph G110, the imaging area 28*a* includes a plurality of scanning areas. In the operation represented in the graph G110, an area 289*a*, an area 289*b*, and an area 289*c* are set as the scanning area. The area 289*a* is disposed on the uppermost side, and the area 289*c* is disposed on the lowermost side. The area 289*b* is disposed between the area 289*a* and the area 289*c*. The area 289*a*, the area 289*b*, and the area 289*c* do not overlap each other. In the second frame period, the illumination control unit 46 controls the illumination unit 29 such that the LED 29*a* is intermittently turned on.

A straight line L110 represents an end timing of resetting, in other words, a start timing of exposure in the pixels 54 of each row disposed in the area 289*a*. A straight line L111 represents a start timing of transmission of electric charge, in other words, an end timing of exposure in the pixels 54 of each row disposed in the imaging area 289*a*. A straight line L112 represents an end timing of resetting, in other words, a start timing of exposure in the pixels 54 of each row disposed in the area 289*b*. A straight line L113 represents a start timing of transmission of electric charge, in other words, an end timing of exposure in the pixels 54 of each row disposed in the imaging area 289*b*. A straight line L114 represents an end timing of resetting, in other words, a start timing of exposure in the pixels 54 of each row disposed in the area 289*c*. A straight line L115 represents a start timing of transmission of electric charge, in other words, an end timing of exposure in the pixels 54 of each row disposed in the imaging area 289*c*. The slope of the straight line L110, the straight line L111, the straight line L112, the straight line L113, the straight line L114, and the straight line L115 is based on the scanning rate. The scanning rate in the second frame period is higher than the scanning rate in the first frame period. An exposure period is a period from a timing represented by the straight line L110, the straight line L112, and the straight line L114 to a timing represented by the straight line L111, the straight line L113, and the straight line L115. The length of the exposure period, in other words, an exposure time is ΔTe7.

In the second frame period, at least parts of the exposure periods of all of the pixels 54 disposed in the area 289*a* overlap each other. In addition, in the second frame period, at least parts of the exposure periods of all of the pixels 54 disposed in the area 289*b* overlap each other. Furthermore, in the second frame period, at least parts of the exposure periods of all of the pixels 54 disposed in the area 289*c* overlap each other. The illumination control unit 46 intermittently turns on the LED 29*a* in a period in which at least parts of the exposure periods of all of the pixels 54 disposed in the area 289*a* overlap each other. Thereafter, the illumination control unit 46 intermittently turns on the LED 29*a* in a period in which at least parts of the exposure periods of all of the pixels 54 disposed in the area 289*b* overlap each other. Thereafter, the illumination control unit 46 intermittently turns on the LED 29*a* in a period in which at least parts of the exposure periods of all of the pixels 54 disposed in the area 289*c* overlap each other. By intermittently turning on the LED 29*b*, a pattern may be projected onto the subject.

The number of rows of each of the area 289*a*, the area 289*b*, and the area 289*c* is less than the number of rows of the imaging area 28*a*. For this reason, an exposure time that is necessary for at least parts of the exposure periods of all of the pixels 54 disposed in each of the area 289*a*, the area 289*b*, and the area 289*c* to overlap each other may be short. The exposure time ΔTe7 of the second frame period is shorter than the exposure time ΔTe5 of the first frame period.

In a case in which the entire imaging area 28*a* is the scanning area, and the exposure period cannot be set such that at least parts of exposure periods of all of the pixels 54 disposed in the scanning area overlap each other, the operation represented in the graph G110 is executed. In this way, the endoscope apparatus 1 can acquire imaging signals of all of the pixels 54 disposed in the scanning area. In the operation represented in the graph G110, the scanning area is divided into the area 289*a*, the area 289*b*, and the area 289*c*. In addition, an exposure period corresponding to each area is set such that at least parts of exposure periods of all of the pixels 54 disposed in each area overlap each other.

In the second frame period, the area 289*a*, the area 289*b*, and the area 289*c* are the scanning area. Resetting, transmission of electric charge, and signal reading are executed in the pixels 54 of all of the rows disposed in the area 289*a*, the area 289*b*, and the area 289*c*. In the second frame period, by using block reading, signal reading may be executed only in the pixels 54 of a part of columns disposed in the area 289*a*, the area 289*b*, and the area 289*c*. In other words, resetting and transmission of electric charge may be executed in the pixels 54 of all of the rows disposed in the area 289*a*, the area 289*b*, and the area 289*c*, and signal reading may be executed only in pixels 54 of a part of columns disposed in the area 289*a*, the area 289*b*, and the area 289*c*.

The measurement processing unit 44 executes the measurement process on the basis of the video signals generated from the imaging signals output from the pixels 54 of the area 289*a*, the area 289*b*, and the area 289*c* in the second frame period. The measurement processing unit 44 notifies a result of the measurement to the graphic image generating unit 43. The graphic image generating unit 43 generates a graphic image signal used for displaying the result of the measurement. The video signal generating unit 41 composes imaging signals output from the pixels 54 of the area 289a, the area 289b, and the area 289c in the second frame period. The video signal generating unit 41 converts the composed imaging signal into a video signal. In this way, the video signal generating unit 41 generates a video signal used for displaying a live image.

In the second frame period, the video signal generated from the imaging signals output from the pixels 54 of the imaging area 28a in the first frame period is output to the signal composing unit 49. In the first frame period, the video signal generated from the imaging signals output from the pixels 54 of the area 289a, the area 289b, and the area 289c in the second frame period is output to the signal composing unit 49. The signal composing unit 49 composes the video signal generated by the video signal generating unit 41 and the graphic image signal generated by the graphic image generating unit 43. The monitor 4 displays an image including the measurement result on the basis of the video signal output from the signal composing unit 49.

In the operation represented in the graph G110, operations of two continuous frame periods are repeatedly executed in a plurality of frame periods. In the operation represented in the graph G110, the image display in each frame period is executed on the basis of video signals generated from imaging signals acquired in the previous frame period. In the operation represented in the graph G110, a measurement result displayed in each frame period is based on the measurement process executed in the second frame period. A measurement result acquired in the second frame period is displayed in two continuous frame periods. In other words, the same measurement result is displayed in two continuous frame periods.

In the operation represented in the graph G110, the exposure time ΔTe7 is shorter than the exposure time ΔTe5. For this reason, the illumination control unit 46 may control the light quantity of the light source in the second frame period to be larger than the light quantity of the light source in the first frame period. Alternatively, the control unit 47 may control a second gain to be larger than a first gain. Here, the second gain is a gain when imaging signals read from the pixels 54 in the second frame period are amplified by the video signal generating unit 41 or the signal processing unit 52. The first gain is a gain when imaging signals read from the pixels 54 in the first frame period are amplified by the video signal generating unit 41 or the signal processing unit 52.

In the operation represented in the graph G110, the control unit 47 sets a plurality of scanning areas (the area 289a, the area 289b, and the area 289c). The imaging element 28 generates a plurality of imaging signals of the pixels 54 corresponding to each of the plurality of scanning areas. The video signal generating unit 41 generates the video signal by composing the plurality of imaging signals of the pixels 54 corresponding to each of the plurality of scanning areas. In this way, the endoscope apparatus 1 can acquire an image corresponding to the entirety of the plurality of scanning areas.

In the operation represented in the graph G110, the imaging element 28 generates the imaging signals of the pixels included in each of the plurality of scanning areas in different periods. In other words, the imaging element 28 generates the imaging signals of the pixels 54 included in each of the area 289a in the first period of the second frame period. Thereafter, the imaging element 28 generates the imaging signals of the pixels 54 included in each of the area 289b in the second period of the second frame period.

Thereafter, the imaging element 28 generates the imaging signals of the pixels 54 included in each of the area 289c in the third period of the second frame period. The order in which the imaging signals are generated is not limited to the order described above. For example, after the imaging signals of the pixels 54 included in each of the area 289a is generated, imaging signals of the pixels 54 included in each of the area 289c may be generated, and thereafter, the imaging signals of the pixels 54 included in each of the area 289b may be generated.

The endoscope apparatus 1 includes the measurement processing unit 44 that executes the measurement process on the basis of the video signal. The plurality of operation modes include an operation mode in which at least the measurement process is executed. In the operation represented in the graph G110, in a case in which an operation mode in which at least the measurement process is executed is set and a plurality of measurement points are set, the control unit 47 sets a plurality of scanning areas to include the pixel 54 at which each of the plurality of measurement points is set. For example, in the operation represented in the graph G110, three measurement points are designated. The area 289a, the area 289b, and the area 289c are set such that the pixels 54 at which the three measurement points are set are included in mutually-different areas. In this way, the endoscope apparatus 1 can acquire an image of an area that is necessary for the measurement process in a case in which a plurality of measurement points are set.

In the operation represented in the graph G110, the observation/measurement mode M2 is set. The imaging signals acquired in the first frame period are used for the image display. The imaging signals acquired in the second frame period are used for the measurement process and the image display. The control unit 47 controls the scanning rate in the second frame period to be larger than the scanning rate in the first frame period. In this way, the endoscope apparatus 1 can acquire more images in the second frame period.

In the operation represented in the graph G110, the imaging area 28a in the second frame period includes three scanning areas. The imaging area 28a in the second frame period may include two scanning areas. The imaging area 28a in the second frame period may include four scanning areas or more.

In the operation represented in the graph G110, imaging and intermittent turning-on of the LED 29a are executed once in each of the area 289a, the area 289b, and the area 289c in the second frame period. Imaging and intermittent turning-on of the LED 29a may be executed two times or more in each of the area 289a, the area 289b, and the area 289c in the second frame period.

In each operation described above, in a case in which an operation mode, in which at least the measurement process is executed, is set, the control unit 47 may set the scanning area to include the pixel 54 at which a measurement point is set. In this way, the endoscope apparatus 1 can acquire an image of an area that is necessary for the measurement process.

In this embodiment, in a case in which a predetermined operation mode is set, the control unit 47 controls the imaging element 28 such that at least parts of exposure periods of pixels 54 disposed in at least a part of the scanning area overlap each other. In a case in which a predetermined operation mode is set, the illumination control unit 46 controls the illumination unit 29 such that the light source is turned on in a period in which at least parts of exposure periods of pixels 54 disposed in at least a part of the scanning area overlap each other. For this reason, the endoscope apparatus 1 can acquire an image in which distortion of the subject is reduced.

In a case in which the predetermined operation mode is set, the control unit 47 may set a scanning area only in a part of the imaging area 28a. For example, in a case in which the observation/measurement mode M2 is set, the control unit 47 sets the scanning area only in a part of the imaging area 28a. In this way, the processing load of the CPU 18 that is necessary for reading imaging signals is reduced.

In a case in which an operation mode, in which at least the measurement process is executed, is set, the light source may be turned on in a period in which at least parts of exposure periods of the pixels 54 disposed in at least a part of the scanning area overlap each other. In this way, the endoscope apparatus 1 can execute the measurement process on the basis of an image in which distortion of the subject is reduced. In other words, the measurement accuracy is improved.

The control unit 47 may control a second gain used for amplifying imaging signals of the pixels 54 corresponding to an incomplete exposure area to be larger than a first gain used for amplifying imaging signals of the pixels 54 corresponding to a complete exposure area. In this way, insufficiency of the exposure amount in the incomplete exposure area is remedied.

Periods in which illumination light is emitted to the subject in the exposure period in all of the pixels 54 disposed in the scanning area may be the same. In such a case, all of the pixels 54 arranged in the scanning area are included in a complete exposure area.

The light source may be intermittently turned on plural times. In a case in which the exposure period cannot be set such that at least parts of exposure periods of all of the pixels 54 disposed in the scanning area overlap each other, by intermittently turning on the light source plural times, the endoscope apparatus 1 can acquire imaging signals of all of the pixels 54 disposed in the scanning area. The light quantities of illumination light in the plural times of turning-on may be the same. In such a case, variations in the exposure amounts of the pixels 54 are reduced.

A first time and a second time may be the same. The first time is a length of a period in which illumination light is emitted to the subject in accordance with intermittent turning-on of the light source once in the exposure period of a complete exposure area. The second time is a sum of a plurality of lengths of periods in which illumination light is emitted to the subject in accordance with plural times of intermittent turning-on of the light source in the exposure period of an incomplete exposure area. In this way, variations in the exposure amount between the pixel 54 of the complete exposure area and the pixel 54 of the incomplete exposure area are reduced.

The video signal generating unit 41 may detect moving of a subject on the basis of imaging signals or video signals corresponding to the pixels 54 of the incomplete exposure area. The endoscope apparatus 1 may generate a warning in a case in which that amount of moving of the subject is a predetermined amount of more. In such a case, a user can notice that blurring has occurred in the subject.

In a case in which an operation mode, in which at least the measurement process is executed, is set, the scanning area may be set to include the pixel 54 at which a measurement point is set. In such a case, the endoscope apparatus 1 can acquire an image of an area that is necessary for the measurement process.

In a case in which a plurality of scanning areas are set, the video signal generating unit 41 may generate a video signal by composing a plurality of imaging signals of the pixels 54 included in each of the plurality of scanning areas. In such a case, the endoscope apparatus 1 can acquire an image for the entirety of the plurality of scanning areas.

In a case in which an operation mode in which at least the measurement process is executed is set and a plurality of measurement points are set, each of a plurality of scanning areas may be set to include the pixel 54 at which each of the plurality of measurement points is set. In such a case, the endoscope apparatus 1 can acquire an image of an area that is necessary for the measurement process in a case in which the plurality of measurement points are set.

In a case in which an operation mode in which at least the measurement process is executed is set, the first scanning rate for acquiring imaging signals used for the measurement process may be set to a value larger than that of the second scanning rate for acquiring imaging signals used only for a process other than the measurement process. In such a case, the endoscope apparatus 1 can acquire an image at a higher frame rate. Alternatively, the endoscope apparatus 1 can acquire more images in the frame period.

In a case in which an operation mode in which at least the image display and the measurement process are executed is set, the imaging element 28 may alternately output a first imaging signal for one image used for the image display and a second imaging signal for one or more images used for the measurement process. In such a case, the endoscope apparatus 1 can execute the measurement process in real time.

In a case in which an operation mode in which at least the image display and the measurement process are executed is set, the imaging element 28 may output a first imaging signal used for the image display in the first frame period and output a second imaging signal used for the measurement process in the second frame period following the first display period. The monitor 4 may display an image on the basis of video signals generated from the first imaging signals in the first frame period and the second frame period. In such a case, the endoscope apparatus 1 can continue to execute the image display.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope apparatus comprising:
   an imaging element configured to generate imaging signals by imaging a subject and include a plurality of pixels disposed in a matrix pattern, an imaging area in which the plurality of pixels are disposed including a scanning area, the imaging signals being read from at least a part of the pixels of each row in the scanning area;
   a video signal generating circuit configured to generate video signals from the imaging signals;
   an illuminator comprising a light source configured to generate illumination light emitted to the subject; and
   one or more processors comprising hardware, wherein the one or more processors are configured to:
   control the imaging element and the illuminator in accordance with a set operation mode among a plurality of operation modes, the plurality of operation modes comprising a first operation mode and a second operation mode;
control the illuminator such that the light source is continuously controlled to be turned on in exposure periods of all of the pixels disposed in the scanning area, in a case in which the first operation mode is set;
control the imaging element such that at least parts of the exposure periods of the pixels disposed in at least a part of the scanning area overlap each other, in a case in which the second operation mode is set; and
control the illuminator such that the light source is turned on in a period in which at least parts of the exposure periods of the pixels disposed in at least a part of the scanning area overlap each other, in a case in which the second operation mode is set.

2. The endoscope apparatus according to claim 1,
wherein the one or more processors are configured to control at least one of a scanning rate, a scanning area, a scanning start timing, an exposure time, and a gain in accordance with the set operation mode.

3. The endoscope apparatus according to claim 1,
wherein the one or more processors are configured to control at least one of a turning-on timing, a turning-on time, and a light quantity of the light source in accordance with the set operation mode.

4. The endoscope apparatus according to claim 1,
wherein the illuminator comprises a plurality of the independent light sources, and
wherein the one or more processors are configured to select the light source that will generate the illumination light in accordance with the set operation mode.

5. The endoscope apparatus according to claim 1,
wherein the one or more processors are configured to execute a measurement process on the basis of the video signal, and
wherein the plurality of operation modes comprise an operation mode in which at least the measurement process is executed.

6. The endoscope apparatus according to claim 5,
wherein the second operation mode is the operation mode in which at least the measurement process is executed.

7. The endoscope apparatus according to claim 5,
wherein a method of driving the imaging element is a rolling shutter,
wherein the video signal generating circuit is configured to generate the video signals by amplifying the imaging signals with a predetermined gain,
wherein the scanning area includes a first area and a second area,
wherein the first area is an area in which a length of a period, in which the illumination light is emitted to the subject in the exposure period, is a first time,
wherein the second area is an area in which a length of a period, in which the illumination light is emitted to the subject in the exposure period, is a second time that is shorter than the first time,
wherein a second gain has a value calculated by dividing the first time by the second time and multiplying a quotient thereof by a first gain,
wherein the second gain is a gain when the imaging signals read from the pixels disposed in the second area are amplified by the video signal generating circuit, and
wherein the first gain is a gain when the imaging signals read from the pixels disposed in the first area are amplified by the video signal generating circuit.

8. The endoscope apparatus according to claim 5,
wherein a method of driving the imaging element is a rolling shutter,
wherein the imaging element further comprises a signal processing circuit configured to amplify the imaging signals output from the plurality of pixels with a predetermined gain,
wherein the scanning area comprises a first area and a second area,
wherein the first area is an area in which a length of a period, in which the illumination light is emitted to the subject in the exposure period, is a first time,
wherein the second area is an area in which a length of a period, in which the illumination light is emitted to the subject in the exposure period, is a second time that is shorter than the first time,
wherein a second gain has a value calculated by dividing the first time by the second time and multiplying a quotient thereof by a first gain,
wherein the second gain is a gain when the imaging signals read from the pixels disposed in the second area are amplified by the signal processing circuit, and
wherein the first gain is a gain when the imaging signals read from the pixels disposed in the first area are amplified by the signal processing circuit.

9. The endoscope apparatus according to claim 5,
wherein the one or more processors are configured to control the illuminator such that the light source is turned on in a period in which at least parts of the exposure periods of all of the pixels disposed in the scanning area overlap each other, and such that periods in which the illumination light is emitted to the subject in all of the pixels disposed in the scanning area in the exposure periods are the same.

10. The endoscope apparatus according to claim 5,
wherein the one or more processors are configured to control the illuminator such that the light source is intermittently turned on plural times, and such that at least parts of the exposure periods of the pixels disposed in at least a part of the scanning area overlap each other in each period of the plural times of turning-on.

11. The endoscope apparatus according to claim 10,
wherein the one or more processors are configured to control the illuminator such that light quantities of the illumination light in the plural times of turning-on are the same.

12. The endoscope apparatus according to claim 11,
wherein in a case in which an emission time is completely included in the exposure periods of first pixels of the scanning area and only a part of the emission time is included in the exposure periods of second pixels of the scanning area, the one or more processors are configured to control the illuminator such that a first time and a second time are the same,
wherein the second pixels are different from the first pixels,
wherein the emission time is a length of a period in which the illumination light is emitted to the subject in accordance with intermittent turning-on of the light source once,
wherein the first time is a length of a period in which the illumination light is emitted to the subject in accordance with intermittent turning-on of the light source once in the exposure periods of the first pixels, and
wherein the second time is a sum of a plurality of lengths of periods in which the illumination light is emitted to the subject in accordance with plural times of intermittent turning-on of the light source in the exposure periods of the second pixels.

13. The endoscope apparatus according to claim 12, further comprising:
a motion detector configured to detect moving of the subject on the basis of the imaging signals read from the second pixels or the video signal generated from the imaging signals read from the second pixels; and
a warning generator configured to generate a warning in a case in which the amount of the moving of the subject is equal to or greater than a predetermined amount.

14. The endoscope apparatus according to claim 5, wherein the one or more processors are configured to set the scanning area to include the pixel at which a measurement point is set in a case in which the operation mode in which at least the measurement process is executed is set.

15. The endoscope apparatus according to claim 1, wherein the one or more processors are configured to set a plurality of scanning areas,
wherein the imaging element is configured to generate the imaging signals of the pixels included in each of the plurality of the scanning areas, and
wherein the video signal generating circuit is configured to generate the video signal by composing the imaging signals of the pixels included in each of the plurality of the scanning areas.

16. The endoscope apparatus according to claim 15, wherein the one or more processors are configured to execute a measurement process on the basis of the video signal,
wherein the plurality of operation modes comprise an operation mode in which at least the measurement process is executed, and
wherein the one or more processors are configured to set each of the plurality of the scanning areas to include the pixel at which each of the plurality of measurement points is set, in a case in which the operation mode in which at least the measurement process is executed is set and a plurality of measurement points are set.

17. The endoscope apparatus according to claim 1, wherein the one or more processors are configured to execute a measurement process on the basis of the video signal,
wherein the illuminator comprises a plurality of the light sources each comprising a measurement light source configured to project a pattern onto the subject,
wherein the plurality of operation modes comprise an operation mode in which at least the measurement process is executed, and
wherein the one or more processors are configured to turn on the measurement light source, in a case in which the operation mode in which at least the measurement process is executed is set.

18. The endoscope apparatus according to claim 5, wherein the one or more processors are configured to control a first scanning rate to be larger than a second scanning rate, in a case where the operation mode in which at least the measurement process is executed is set,
wherein the first scanning rate is a scanning rate for reading the imaging signals used for the measurement process from the pixels, and
wherein the second scanning rate is a scanning rate for reading the imaging signals used only for a process other than the measurement process from the pixels.

19. The endoscope apparatus according to claim 1, further comprising:
a display configured to display an image of the subject,
wherein the one or more processors are configured to execute a measurement process on the basis of the video signal,
wherein the plurality of operation modes comprise an operation mode in which at least image display and the measurement process are executed,
wherein the one or more processors are configured to control the imaging element to alternately output a first imaging signal and a second imaging signal, in a case where the operation mode in which at least the image display and the measurement process are executed is set,
wherein the first imaging signal is for one image used for the image display,
wherein the second imaging signal is for one or more images used for the measurement process,
wherein the display is configured to display the one image on the basis of the video signal generated from the first imaging signal, and
wherein the one or more processors are configured to execute the measurement process on the basis of the video signal generated from the second imaging signal and corresponding to the one or more images.

20. The endoscope apparatus according to claim 19, wherein the one or more processors are configured to control the imaging element to output the first imaging signal in a first display period and output the second imaging signal in a second display period following the first display period,
wherein the first display period and the second display period are based on a display period of the display, and
wherein the display displays the one image on the basis of the video signal generated from the first imaging signal in the first display period and the second display period.

21. A method of operating an endoscope apparatus, the method comprising:
a first step;
a second step; and
a third step,
wherein the endoscope apparatus includes:
an imaging element configured to generate imaging signals by imaging a subject and include a plurality of pixels disposed in a matrix pattern, an imaging area in which the plurality of pixels are disposed including a scanning area, the imaging signals being read from at least a part of the pixels of each row in the scanning area;
a video signal generating circuit configured to generate video signals from the imaging signals;
an illuminator comprising a light source configured to generate illumination light emitted to the subject; and
one or more processors comprising hardware, and
wherein the method comprises:
controlling, by the one or more processors, the imaging element and the illuminator in accordance with a set operation mode among a plurality of operation modes, the plurality of operation modes comprising a first operation mode and a second operation mode;
controlling, by the one or more processors, the illuminator such that the light source is continuously controlled to be turned on in exposure periods of all of the pixels disposed in the scanning area in the first step, in a case in which the first operation mode is set;

controlling, by the one or more processors, the imaging element such that at least parts of the exposure periods of the pixels disposed in at least a part of the scanning area overlap each other in the second step, in a case in which the second operation mode is set; and controlling, by the one or more processors, the illuminator such that the light source is turned on in a period in which at least parts of the exposure periods of the pixels disposed in at least a part of the scanning area overlap each other in the third step, in a case in which the second operation mode is set.

22. A non-transitory computer-readable recording medium having a program for operating an endoscope apparatus to execute a first step, a second step, and a third step recorded thereon, the endoscope apparatus comprising:
an imaging element configured to generate imaging signals by imaging a subject and include a plurality of pixels disposed in a matrix pattern, an imaging area in which the plurality of pixels are disposed including a scanning area, the imaging signals being read from at least a part of the pixels of each row in the scanning area;
a video signal generating circuit configured to generate video signals from the imaging signals;
an illuminator comprising a light source configured to generate illumination light emitted to the subject; and
the one or more processors, wherein the program causes the one or more processors to:
control the imaging element and the illuminator in accordance with a set operation mode among a plurality of operation modes, the plurality of operation modes comprising a first operation mode and a second operation mode;
control the illuminator such that the light source is continuously controlled to be turned on in exposure periods of all of the pixels disposed in the scanning area in the first step, in a case in which the first operation mode is set;
control the imaging element such that at least parts of the exposure periods of the pixels disposed in at least a part of the scanning area overlap each other in the second step, in a case in which the second operation mode is set; and
control the illuminator such that the light source is turned on in a period in which at least parts of the exposure periods of the pixels disposed in at least a part of the scanning area overlap each other in the third step, in a case in which the second operation mode is set.

* * * * *